(12) United States Patent
Davis et al.

(10) Patent No.: US 6,835,378 B2
(45) Date of Patent: Dec. 28, 2004

(54) METHOD AND COMPOSITIONS FOR INHIBITING THROMBIN-INDUCED COAGULATION

(75) Inventors: Stacey Davis, College Station, TX (US); Magnus A. O. Hook, Houston, TX (US)

(73) Assignee: The Texas A&M University System University, College Station, TX (US)

( * ) Notice: Subject to any disclaimer, the term of this patent is extended or adjusted under 35 U.S.C. 154(b) by 0 days.

(21) Appl. No.: 10/142,935

(22) Filed: May 13, 2002

(65) Prior Publication Data

US 2003/0044418 A1 Mar. 6, 2003

Related U.S. Application Data

(60) Provisional application No. 60/290,072, filed on May 11, 2001.

(51) Int. Cl.$^7$ ................................................ A61K 38/48
(52) U.S. Cl. ................................ 424/94.63; 424/94.63; 424/94.67; 530/382; 514/2; 514/15
(58) Field of Search .......................... 424/44.63, 14.64, 424/94.67, 94.63; 514/2, 12, 13, 14, 15; 530/382

(56) References Cited

U.S. PATENT DOCUMENTS

| | | |
|---|---|---|
| 5,175,096 A | 12/1992 | Hook et al. |
| 5,320,951 A | 6/1994 | Hook et al. |
| 5,416,021 A | 5/1995 | Hook et al. |
| 5,440,014 A | 8/1995 | Hook et al. |
| 5,571,514 A | 11/1996 | Hook et al. |
| 5,652,217 A | 7/1997 | Hook et al. |
| 5,707,702 A | 1/1998 | Brady, Jr. et al. |
| 5,789,549 A | 8/1998 | Hook et al. |
| 5,840,846 A | 11/1998 | Hook et al. |
| 5,851,794 A | 12/1998 | Guss et al. |
| 5,980,908 A | 11/1999 | Hook et al. |
| 6,008,341 A | 12/1999 | Foster et al. |
| 6,086,895 A | 7/2000 | Hook et al. |
| 6,177,084 B1 | 1/2001 | Foster et al. |
| 6,288,214 B1 | 9/2001 | Hook et al. |

OTHER PUBLICATIONS

Mannis M. J. 2001, Transactions of the American Ophthalmological Society, vol. 99 pp. 243–271.*
Wann et al., "The Fibronectin–binding MSCRAMM FnbpA of *Staphylococcus aureus* Is a Bifunctional Protein That Also Binds to Fibrinogen", The Journal of Biological Chemistry, Vo. 275, No. 18, May 15, 2000, pp. 13863–13871.

Pei et al., "Functional Studies of a Fibrinogen Binding Protein from *Staphylococcus epidermidis*", Infection and Immunity, vol. 67, No. 9, Sep. 1999, pp. 4525–4530.

Shainoff et al., "Fibrinopeptide B and Aggregation of Fibrinogen", Science vol. 204, Apr. 13, 1979, pp. 200–202.

Hartford et al., "The Fbe(SdrG) protein of *Staphylococcus epidermidis* HB promotes bacterial adherence to fibrinogen", Microbiology (2001), 147, pp. 2545–2552.

McCrea et al., "The serine–aspartate repeat (Sdr) protein family in *Staphylococcus epidermidis*", Microbiology (2000), 146, pp. 1535–1546.

Davis et al., "SdrG, a Fibrinogen–binding Bacterial Adhesion of the Microbial Surface Components Recognizing Adhesive Matrix Molecules . . . ", The Journal of Biological Chemistry, vol. 276, No. 30, Issue of Jul. 27, pp. 22799–27805, 2001.

* cited by examiner

Primary Examiner—Christopher R. Tate
Assistant Examiner—B. Dell Chism
(74) Attorney, Agent, or Firm—Stites & Harbison PLLC; B. Aaron Schulman

(57) ABSTRACT

A method of achieving safe and effective treatment or prevention of potentially harmful blood clots, or in inhibiting the coagulation of blood when so desired such as during a wide array of disease conditions including stroke, myocardial infarction, sickle-cell crisis and venous thrombosis, is provided by the administration of a fibrinogen-binding protein capable of binding at the N-terminal Bβ chain of fibrinogen, such as SdrG or Fbe, or their respective binding regions such as the A domain. In addition, compositions comprising effective amounts of the fibrinogen-binding proteins are also provided. The present anti-coagulation compositions have been shown to inhibit thrombin-induced fibrin clot formation by interfering with the release of fibrinopeptide B and the resulting anti-coagulation effects can be achieved without potential for causing or exacerbating unwanted side effects such as thrombocytopenia associated with prior art anticoagulants such as heparin.

13 Claims, 13 Drawing Sheets

SEQUENCE LISTING

<160> NUMBER OF SEQ ID NOS: 11

<210> SEQ ID NO 1
<211> LENGTH: 5
<212> TYPE: PRT
<213> ORGANISM: Staphylococcus epidermidis
<220> FEATURE:
<221> NAME/KEY: MISC_FEATURE
<222> LOCATION: (3)..(3)
<223> OTHER INFORMATION: X = any amino acid

<400> SEQUENCE: 1

Leu Pro Xaa Thr Gly
1               5

<210> SEQ ID NO 2
<211> LENGTH: 31
<212> TYPE: DNA
<213> ORGANISM: Staphylococcus epidermidis

<400> SEQUENCE: 2
cccggatccg aggagaatac agtacaagac g                                      31

<210> SEQ ID NO 3
<211> LENGTH: 33
<212> TYPE: DNA
<213> ORGANISM: Staphylococcus epidermidis

<400> SEQUENCE: 3
cccggtaccg attttttcag gaggcaagtc acc                                    33

<210> SEQ ID NO 4
<211> LENGTH: 25
<212> TYPE: PRT
<213> ORGANISM: Staphylococcus epidermidis

<400> SEQUENCE: 4

Gln Gly Val Asn Asp Asn Glu Glu Gly Phe Phe Ser Ala Arg Gly His
1               5                   10                  15

Arg Pro Leu Asp Lys Lys Arg Glu Glu
            20                  25

<210> SEQ ID NO 5
<211> LENGTH: 20
<212> TYPE: PRT
<213> ORGANISM: Staphylococcus epidermidis

<400> SEQUENCE: 5

Gln Gly Val Asn Asp Asn Glu Glu Gly Phe Phe Ser Ala Arg Gly His
1               5                   10                  15

Arg Pro Leu Asp
            20

<210> SEQ ID NO 6
<211> LENGTH: 20
<212> TYPE: PRT
<213> ORGANISM: Staphylococcus epidermidis

<400> SEQUENCE: 6

Asn Glu Glu Gly Phe Phe Ser Ala Arg Gly His Arg Pro Leu Asp Lys
1               5                   10                  15

Lys Arg Glu Glu

-continued

```
<210> SEQ ID NO 7
<211> LENGTH: 25
<212> TYPE: PRT
<213> ORGANISM: Staphylococcus epidermidis

<400> SEQUENCE: 7

Phe Ser Glu Arg Lys Asp Leu His Gln Gly Glu Gly Asn Pro Arg Glu
1               5                   10                  15

Phe Val Glu Asn Asp Ala Lys Gly Arg
            20                  25

<210> SEQ ID NO 8
<211> LENGTH: 15
<212> TYPE: PRT
<213> ORGANISM: Staphylococcus epidermidis

<400> SEQUENCE: 8

Asn Glu Glu Gly Phe Phe Ser Ala Arg Gly His Arg Pro Leu Asp
1               5                   10                  15

<210> SEQ ID NO 9
<211> LENGTH: 10
<212> TYPE: PRT
<213> ORGANISM: Staphylococcus epidermidis

<400> SEQUENCE: 9

Phe Ser Ala Arg Gly His Arg Pro Leu Asp
1               5                   10

<210> SEQ ID NO 10
<211> LENGTH: 17
<212> TYPE: PRT
<213> ORGANISM: Staphylococcus epidermidis

<400> SEQUENCE: 10

Ala Asp Ser Glu Gly Glu Gly Asp Phe Leu Ala Glu Gly Gly Val
1               5                   10                  15

Arg

<210> SEQ ID NO 11
<211> LENGTH: 14
<212> TYPE: PRT
<213> ORGANISM: Staphylococcus epidermidis

<400> SEQUENCE: 11

Gln Gly Val Asn Asp Asn Glu Glu Gly Phe Phe Ser Ala Arg
1               5                   10
```

METHOD AND COMPOSITIONS FOR INHIBITING THROMBIN-INDUCED COAGULATION

CROSS-REFERENCE TO RELATED APPLICATIONS

Figure 1:
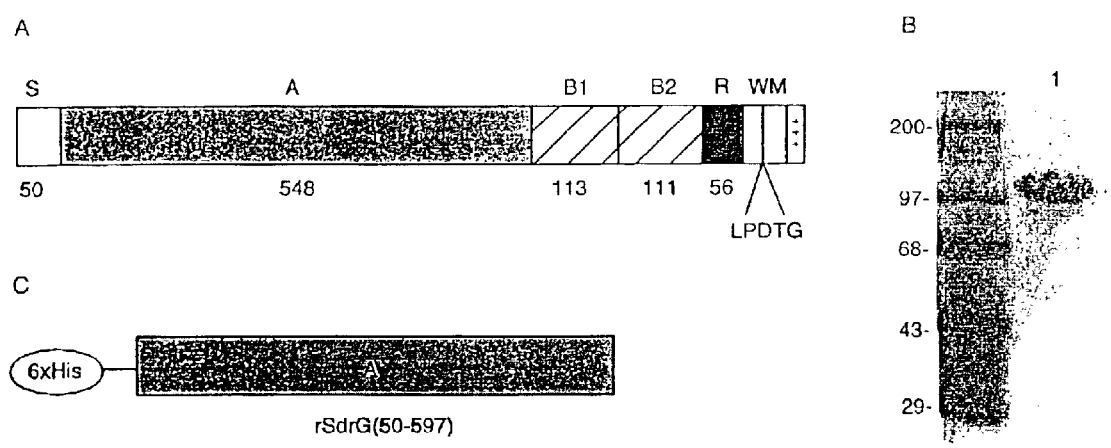

This application claims the benefit of U.S. Provisional Patent Application No. 60/290,072, filed May 11, 2001.

STATEMENT REGARDING FEDERALLY SPONSORED RESEARCH OR DEVELOPMENT

The subject matter of this application was supported by Grant No. AI20624 from the National Institutes of Health.

FIELD OF THE INVENTION

The present invention relates in general to SdrG, a fibrinogen-binding bacterial adhesin, and in particular to the use of SdrG or its binding region as an anti-coagulation agent by virtue of its ability to inhibit thrombin-induced fibrin clot formation by interfering with the release of fibrinopeptide B. In addition, the invention relates to methods and compositions utilizing SdrG or its binding region for treating or preventing thrombin-induced coagulation and conditions associated therewith.

BACKGROUND OF THE INVENTION

Coagulase-negative staphylococci (CNS) are important opportunistic pathogens that are particularly associated with foreign body infections in humans. *Staphylococcus epidermidis* is the most common pathogenic species of CNS and accounts for 74–92% of the infections caused by this group of staphylococci (1). The molecular pathogenesis of most infections is complex and involves multiple microbial factors and host components, but is generally initiated by the adherence of the microbe to host tissues. Bacterial adherence involves specific surface components called adhesins, and bacterial pathogens, such as staphylococci that live in the extracellular space of the host, target extracellular matrix (ECM) components, including fibrinogen (Fg) and fibronectin, for adherence and colonization. This process is mediated by a sub-family of adhesins that have been termed MSCRAMM®s (microbial surface components recognizing adhesive matrix molecules) (2). *Staphylococcus aureus* expresses multiple MSCRAMM®s of which several have been characterized in some detail (For a recent review see Ref. 3), and various MSCRAMM®s have been the subject of U.S. Patents, including fibronectin binding proteins such as disclosed in U.S. Pat. Nos. 5,175,096; 5,320,951; 5,416,021; 5,440,014; 5,571,514; 5,652,217; 5,707,702; 5,789,549; 5,840,846; 5,980,908; and 6,086,895; fibrinogen binding proteins such as disclosed in U.S. Pat. Nos. 6,008,341 and 6,177,084; and collagen binding proteins as disclosed in U.S. Pat. Nos. 5,851,794 and 6,288,214; all of these patents incorporated herein by reference. In addition, other information concerning SdrG and other MSCRAMM®s can be found in U.S. Ser. No. 09/810,428, filed Mar. 19, 2001, incorporated herein by reference; and U.S. Ser. No. 09/386,962, filed Aug. 31, 1999, incorporated herein by reference.

In addition to *S. epidermidis*, *S. aureus* also causes serious foreign body infections. *S. aureus* appears to adhere to the biomaterial through an indirect mechanism. Upon implantation, the foreign body rapidly becomes coated with host proteins derived primarily from plasma with Fg being a dominant component. *S. aureus* appears to adhere to the absorbed proteins rather than to the biomaterial itself using adhesins of the MSCRAMM® family (4,5). At least four of the *S. aureus* MSCRAMM®s recognize Fg. Two of these MSCRAMM®s, clumping factor A and B (ClfA, ClfB), have Fg-binding A-regions followed by a long segment of Ser-Asp (SD) dipeptide repeats. The other two Fg-binding MSCRAMM®s, contain a similar ligand binding A-region followed by a fibronectin binding motif that is repeated 5 times (6). Because the fibronectin binding activity was identified first, these two MSCRAMM®s are known as fibronectin binding protein A and B (FnbpA and FnbpB) (7,8). Studies have demonstrated the importance of ClfA and ClfB in the adherence of *S. aureus* to plasma-coated biomaterials. *S. aureus* mutants deficient in one or both of these MSCRAMM®s exhibited an impaired ability to adhere to plasma-coated catheters in vivo or ex vivo (9,10).

For *S. epidermidis*, adherence to foreign bodies appears to involve both specific and non-specific processes. The bacteria may initially associate directly with the foreign body through non-specific interactions, while the later stages of adherence may involve more specific interactions between bacterial adhesins and host ligands. *S. epidermidis* expresses polysaccharide adhesins including PS/A and PIA, which are encoded by the ica locus (11, 12). In addition, the present inventors (13) and others (14) have recently shown that *S. epidermidis* contains surface proteins structurally related to *S. aureus* MSCRAMM®s. Two of these *S. epidermidis* proteins, called SdrF and SdrG, have features typical of Gram-positive bacterial proteins that are anchored to the cell wall. Both proteins show significant amino acid sequence homology to ClfA and ClfB from *S. aureus* including an ~500 amino acid long A region, a SD dipeptide repeat region and features required for cell wall anchoring, including a LPXTG (SEQ ID NO:1) motif (FIG. 1A). Recent studies by Pei, et al. suggest that another *S. epidermidis* protein, called Fbe, can bind Fg and, much like SdrG, specifically recognizes the Bβ chain of this molecule (15). However, this reference does not disclose or suggest the specific binding site for the Fbe protein on fibrinogen and thus does not disclose or suggest that the binding site for this protein would be related to of affect in any manner the binding site for thrombin on fibrinogen.

Of these proteins from *S. epidermidis*, SdrG is of particular interest for its ability to bind Fg. Fg is known to play a critical role in the formation of blood clots, although previously the precise binding site of SdrG to Fg has not been localized with specificity. Accordingly, because the precise binding site for SdrG in the Fg Bβ chain has not been localized, it has not been previously been associated with the thrombin cleavage site on fibrinogen and thus it has not previously been recognized or suggested that SdrG might be useful in inhibiting the thrombin-induced cleavage of fibrinogen and the thrombin-induced process of clot formation.

In general, the blood clots generated by Fg, e.g. through its cleavage by thrombin to form fibrin and start the process of blood coagulation, are beneficial in the normal wound healing process. However, abnormal clots caused by the cleavage of Fg can lead to thrombosis, a condition where a clot develops in the circulatory system. Thrombosis is an extremely dangerous condition and may produce ischemic necrosis of the tissue supplied by the artery, e.g., myocardial infarction due to thrombosis of a coronary artery, or stroke due to thrombosis of a cerebral artery. In addition to the above, venous thrombosis may cause the tissues drained by the vein to become edematous and inflamed, and thrombosis of a deep vein may result in a pulmonary embolism. Still other problems result in sickle-cell patients wherein the malformed "sickle cells" can also lead to a sickle-cell crisis state in which coagulation reaches dang once again result in serious injury or even death.

Generally, anticoagulant agents such as heparin and its derivatives are used to treat thrombosis and to prevent or reduce coagulation when desirable such as in the case of myocardial infarction and the other conditions discussed above. Heparin works by inhibiting thrombin generation and in antagonizing thrombin's action. However, the use of heparin has distinct problems which have yet to be overcome. One disadvantage associated with heparin is that it can only be administered parenterally. Another serious disadvantage is major bleeding occurs in 1% to 33% of patients who receive various forms of heparin therapy. In fact, purpura, ecchymoses, hematomas, gastrointestinal hemorrhage, hematuria, and retroperitoneal bleeding are regularly encountered complications of heparin therapy. In addition to the above complications, thrombocytopenia occurs in 1% to 5% of patients receiving heparin.

Accordingly, there is thus a distinct and growing need to provide alternatives to heparin as anti-coagulation agent which do not suffer from all of the above-mentioned side effects or disadvantages. One such alternative is the use of snake venom products including ancrod, an α-fibrinogenase isolated from Calloselasma rhodostoma (Malayan Pit viper). However, ancrod appears to release only FpA and leads to the formation of an unstable fibrin clot (Bell 1997). Moreover, because this defibrinating enzyme cleaves FpA and not FpB from Fg, it forms a clot that is very sensitive to endogenous fibrinolysis, and additionally activates plasminogen further contributing to fibrinolysis (Pizzo, Schwartz et al. 1972; Carr 1975; Bell 1997). Hypofibrinogenemia, i.e., the reduction of Fg in the blood, must be sustained by administering a treatment, the plasma Fg rises and returns to normal levels in days (Bell, Bolton et al. 1968). The limited clinical experience indicates that which defibrination may be achieved with ancrod, the elaboration of neutralizing antibodies with repeated injections of ancrod leads to resistance (see, e.g., Pitney, Holt et al. 1969; Pitney and Regoeczi 1970), (Vinazzer 1973; Sapru, Moza et al. 1975) .

In short, there is a distinct and acute need to provide a safe and effective alternative to the use of heparin in achieving the inhibition in blood coagulation in cases wherein such inhibition may be crucial in saving the life of a human or animal patient.

SUMMARY OF THE INVENTION

It is thus an object of the present invention to provide safe and effective alternatives to the use of heparin in achieving therapeutic anti-coagulant treatment in human and animal patients.

It is further an object of the present invention to provide methods of utilizing fibrinogen-binding proteins from S. epidermidis in the prevention or treatment of thrombin-induced coagulation in human or animal patients.

It is further an object of the present invention to provide methods of utilizing fibrinogen-binding proteins from S. epidermidis in order to reduce or prevent thrombin-induced coagulation and to enhance the dissolution of blood clots in human or animal patients.

It is another object of the invention to provide therapeutic compositions based on fibrinogen-binding proteins from S. epidermidis which bind to the Bβ chain of fibrinogen which are useful in preventing or treating thrombin-induced coagulation in human or animal patients in need thereof.

It is still further an object of the present invention to develop compositions from fibrinogen-binding proteins from S. epidermidis which bind to the Bβ chain of fibrinogen, and which can block the thrombin binding site on fibrinogen so as to be useful in methods of preventing cleavage of fibrinogen by thrombin and inhibiting the release of fibrinopeptide B from fibrinogen.

These and other objects are provided by virtue of the present invention which comprises compositions and methods which utilize the SdrG protein from S. epidermidis, and other proteins which bind to the Bβ chain of fibrinogen such as the A region of SdrG and the Fbe protein, in order to treat or prevent thrombin-induced coagulation in human or animal patients. In addition, the invention comprises methods of administering SdrG so as to treat or prevent a wide variety of conditions wherein blood coagulation can be dangerous or even life-threatening coagulation, including venous thrombosis, myocardial infarction and sickle cell crisis episodes. The invention utilizes the ability of SdrG to inhibit thrombin-induced fibrin clot formation by inhibiting thrombin binding to fibrinogen and interfering with the release of fibrinopeptide B, and therapeutic compositions containing an effective amount of SdrG can thus be used as effective anti-coagulation agents. The SdrG compounds and compositions of the present invention may also be used to reduce the concentration of plasma fibrinogen in a patient's blood when so desired.

These embodiments and other alternatives and modifications within the spirit and scope of the disclosed invention are described in, or will become readily apparent from, reference to the detailed description of the preferred embodiments provided herein below.

BRIEF DESCRIPTION OF THE DRAWING FIGURES

FIG. 1 is a representation of the structural organization of SdrG wherein FIG. 1A is a representation of SdrG. The number of amino acid residues contained in each region is indicated below each segment. S, signal sequence, A, N-terminal Fg binding region, B1 & B2, repeats of unknown function, R, serine-aspartate repeat region, W, wall-spanning region, M, membrane-spanning region. The positively-charged tail and LPXTG motif involved in cell-wall anchoring are also indicated; FIG. 1B is a model of the recombinant His-tag construct rSdrG(50–597), representing the A region; and FIG. 1C shows a Coomasie stained SDS-PAGE of purified rSdrG(50–597).

Figure 2:
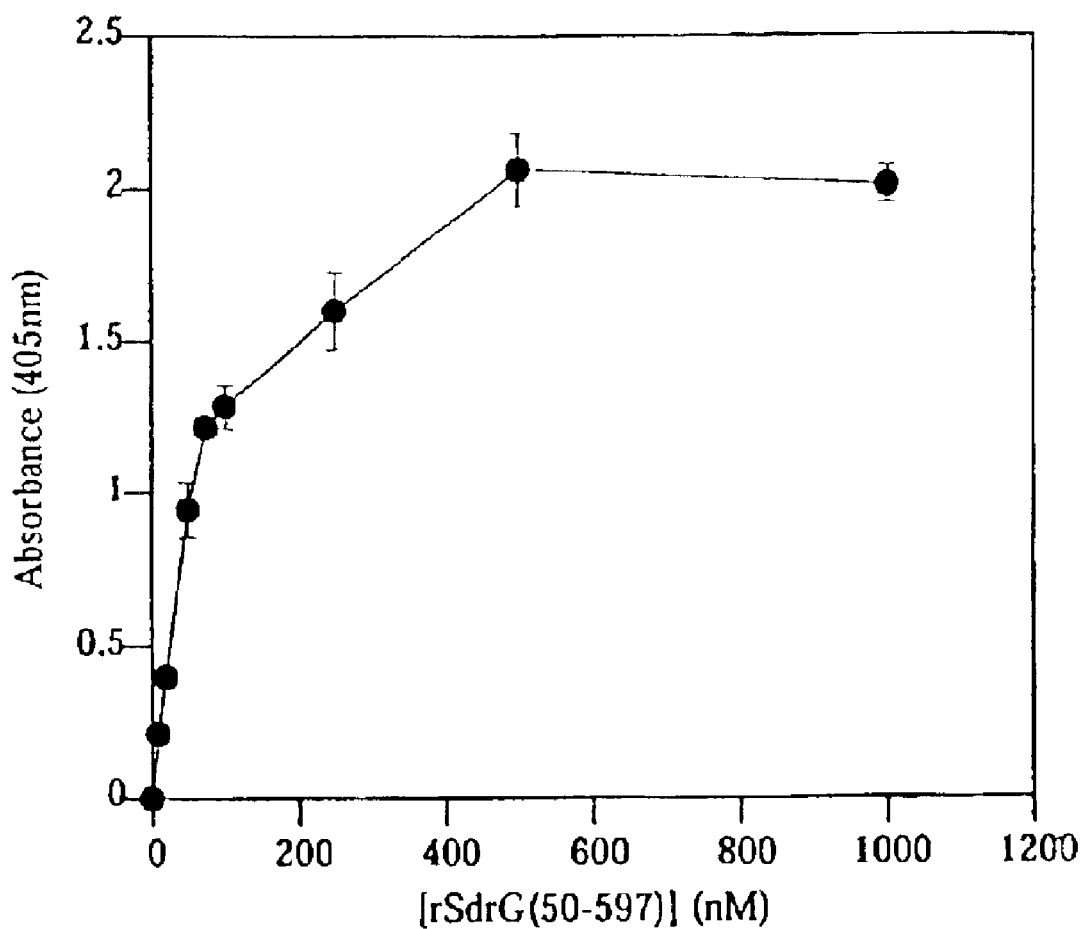

FIG. 2 is a graphic representation of tests showing rSdrG (50–597) binding to immobilized Fg. Increasing concentrations of rSdrG(50–597) (•) were incubated with immobilized Fg in an ELISA. After incubation in the wells for 1 h at room temperature, bound protein was detected as described in the materials and method section. The apparent $K_D$ was $0.9 \times 10^{-7}$ M. Values represent the mean±standard deviation of triplicate wells.

Figure 3:
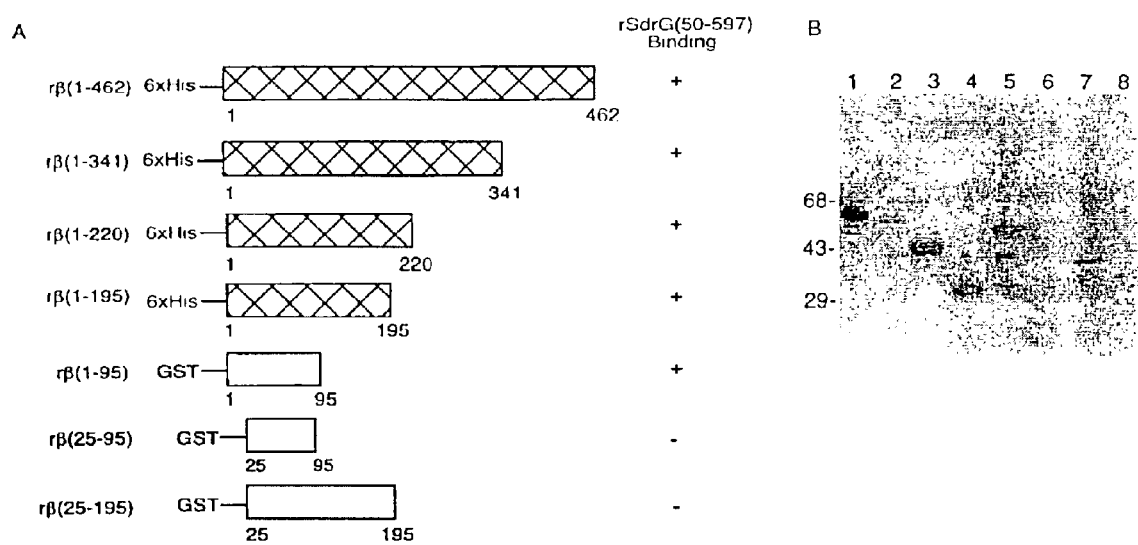

FIG. 3 is a graphic representation of tests showing localization of the rSdrG(50–597) binding site in Fg using recombinant Bβ chain constructs in accordance with the invention. In FIG. 3A, models of the recombinant truncates of the Fg Bβ chain constructed using the pQE30 His-tag vector or the GST fusion vector PGEX-KG are shown. In FIG. 3B, whole E. coli cell lysates containing the recombinant proteins were loaded onto a 10% SDS-polyacrylamide gel. The gel was transferred to a nitrocellulose membrane and the blot was probed with biotin labeled rSdrG(50–597) and developed as described in the materials and methods section. Lane 1, native Fg, lane 2, rβ(1–462), lane 3, rβ(1–341), lane 4, rβ(1–220), lane 5, rβ(1–195), lane 6, rβ(25–195), lane 7, rβ(1–95), lane 8, rβ(25–95).

Figure 4A:
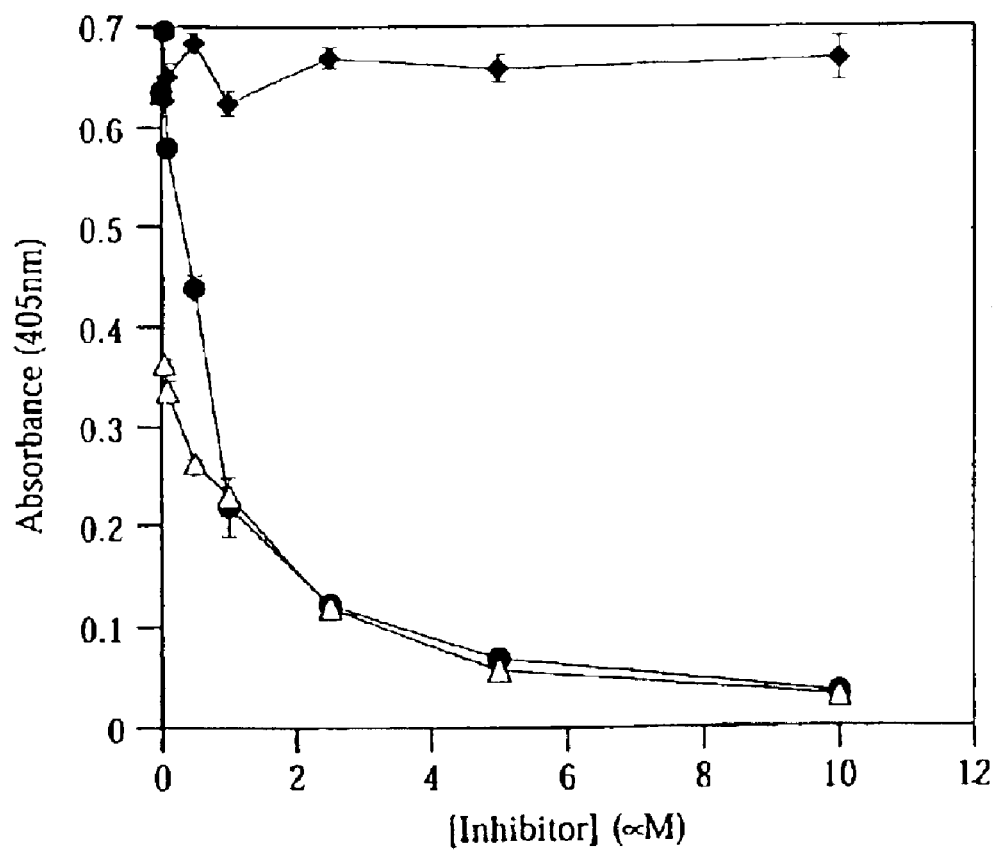
Figure 4B:
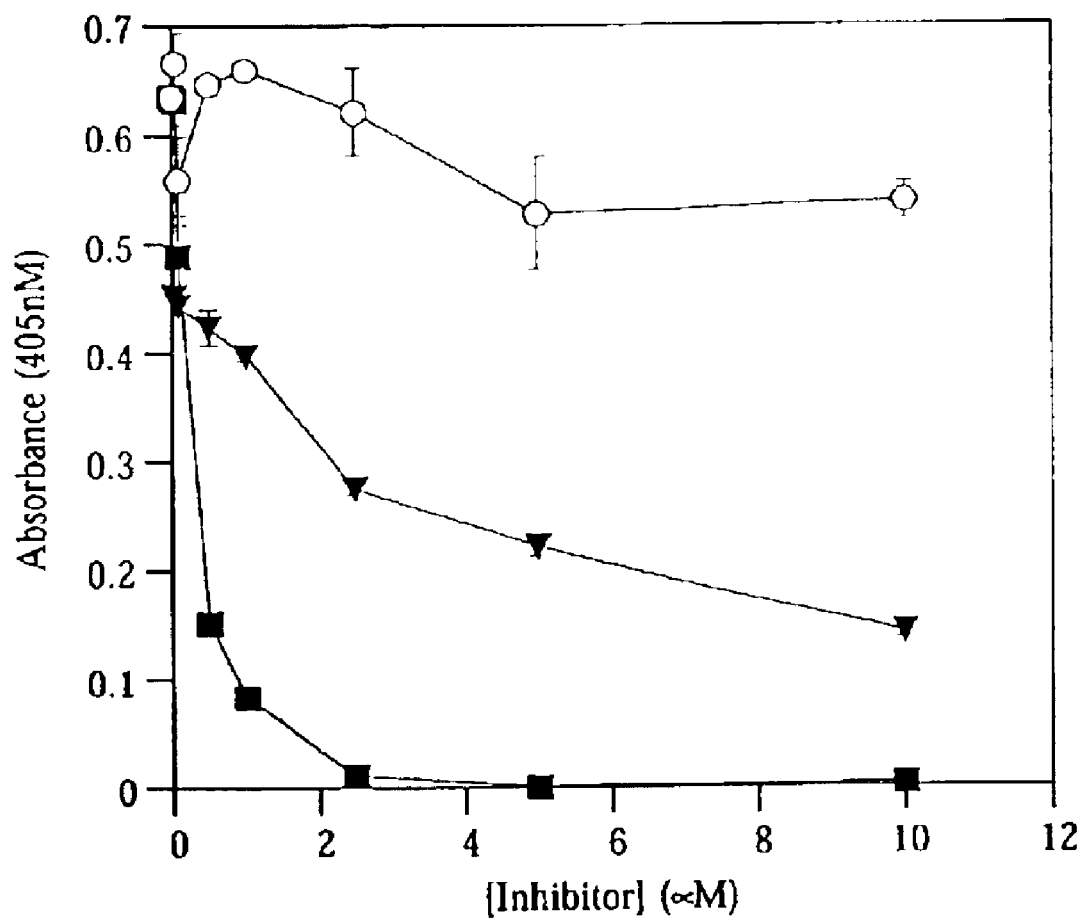
Figure 4C:
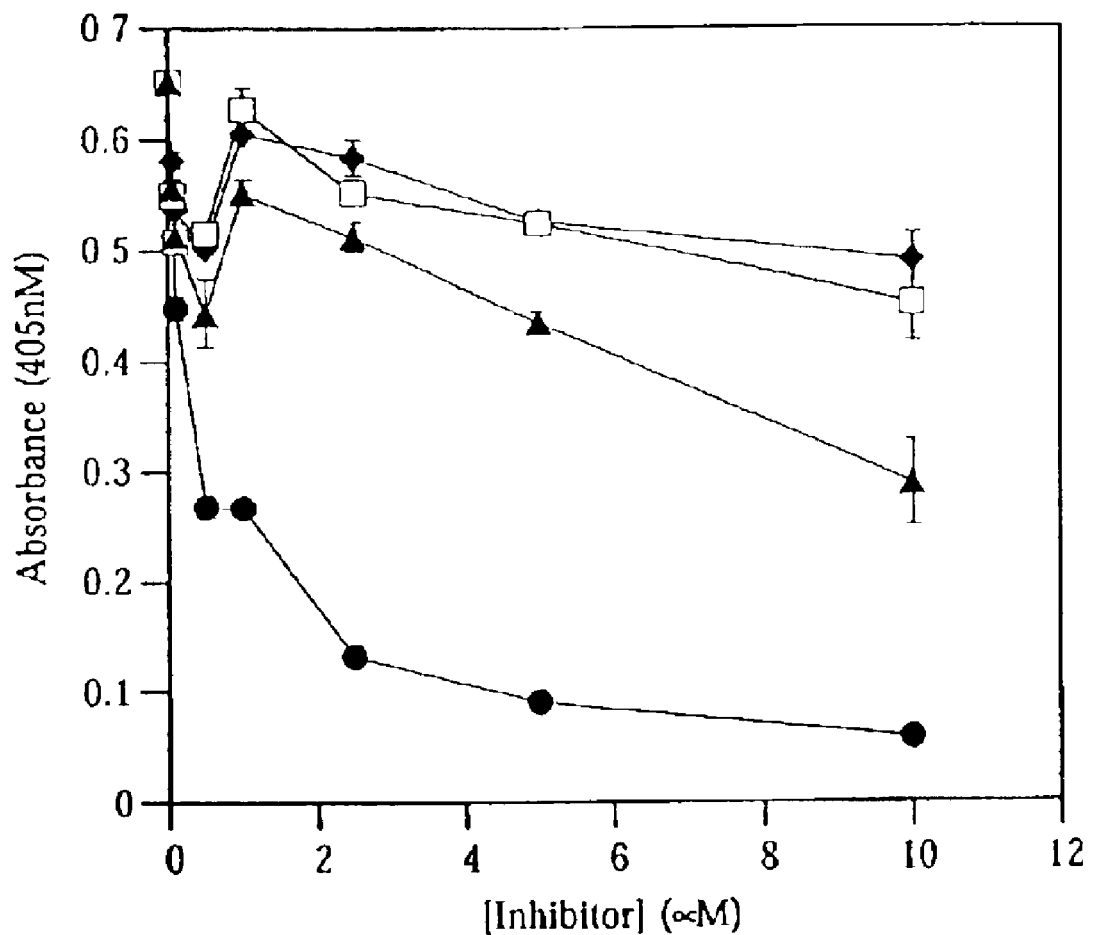

FIG. 4 shows results of tests indicating inhibition of rSdrG(50–597) binding to immobilized Fg by synthetic peptides in accordance with the present invention. In these tests, rSdrG(50–597) (50 nM) was pre-incubated with increasing concentrations of peptides for 1 h at room temperature and transferred to microtiter wells coated with 1 µg human Fg. After incubation in the wells for 1 h at room temperature, bound SdrG was detected as described in the materials and methods section. For FIG. 4A: β1–25 (•), β6–25 (Δ), β1–25S (♦); FIG. 4B: β6–20 (■), β1–20 (▲) and β11–20 (○). For FIG. 4C: FpA (□), FpB (▲), β1–25 (•), β1–25S (♦). Values represent the mean±standard deviation of triplicate wells.

Figure 5:
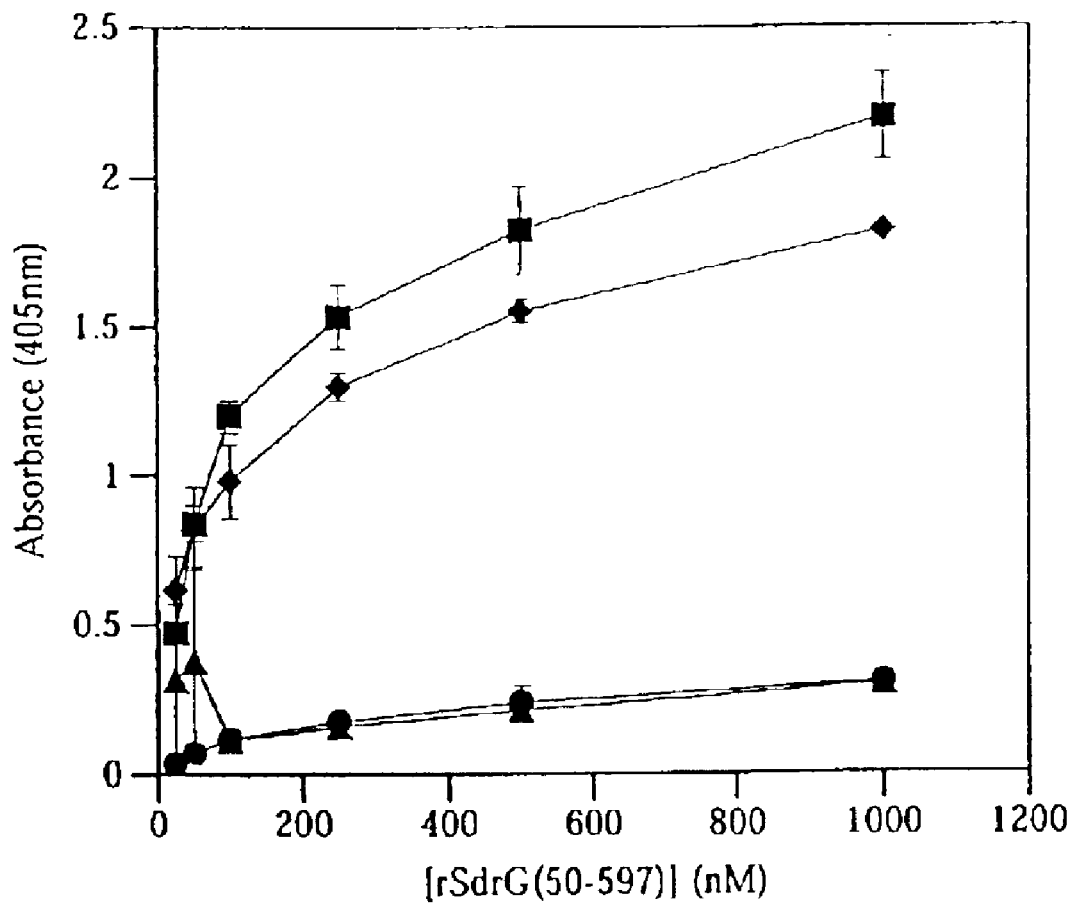

FIG. 5 shows rSdrG(50–597) binding to thrombin digested Fg. Fg coated microtiter wells were pretreated for 30 min at 37° C. with thrombin (▼), thrombin and hirudin (•), hirudin alone (♦) or untreated (■). Plates were blocked, washed and incubated with biotin labeled rSdrG(50–597) (25–1000 nM) for 1 h at room temperature. Bound SdrG was detected as described in materials and methods. Values represent the mean±standard deviation of triplicate wells.

Figure 6A:
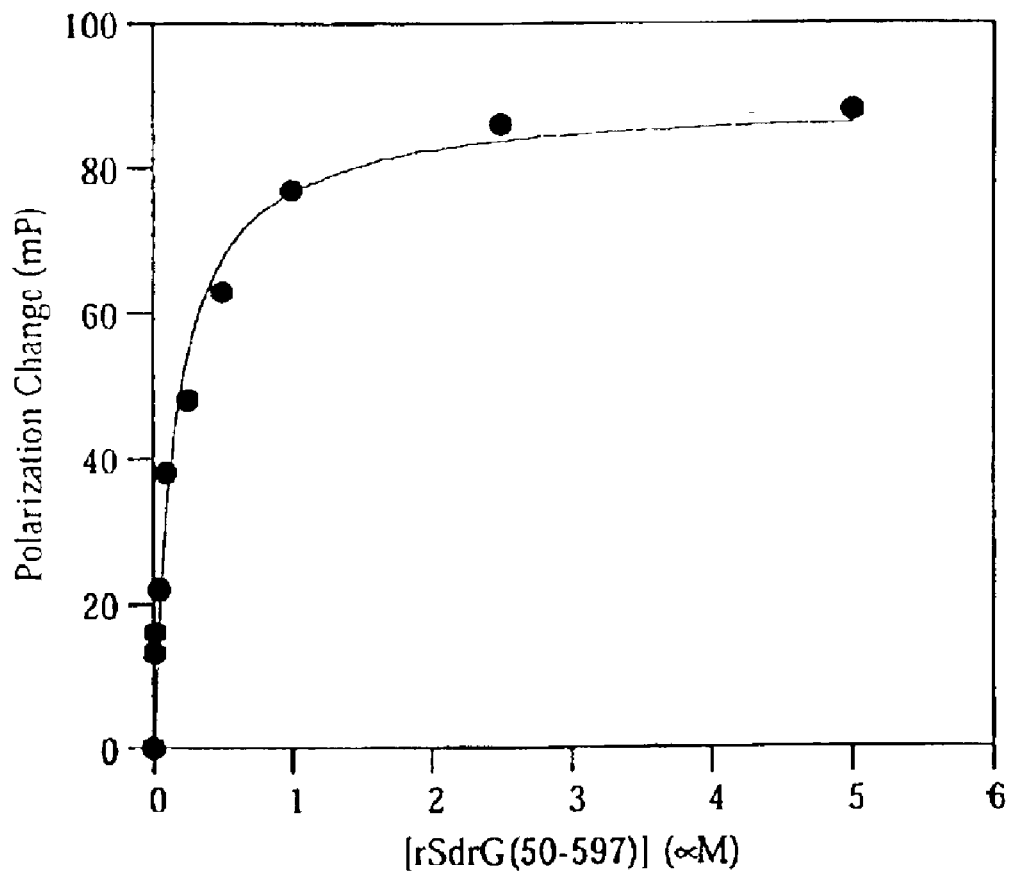
Figure 6B:
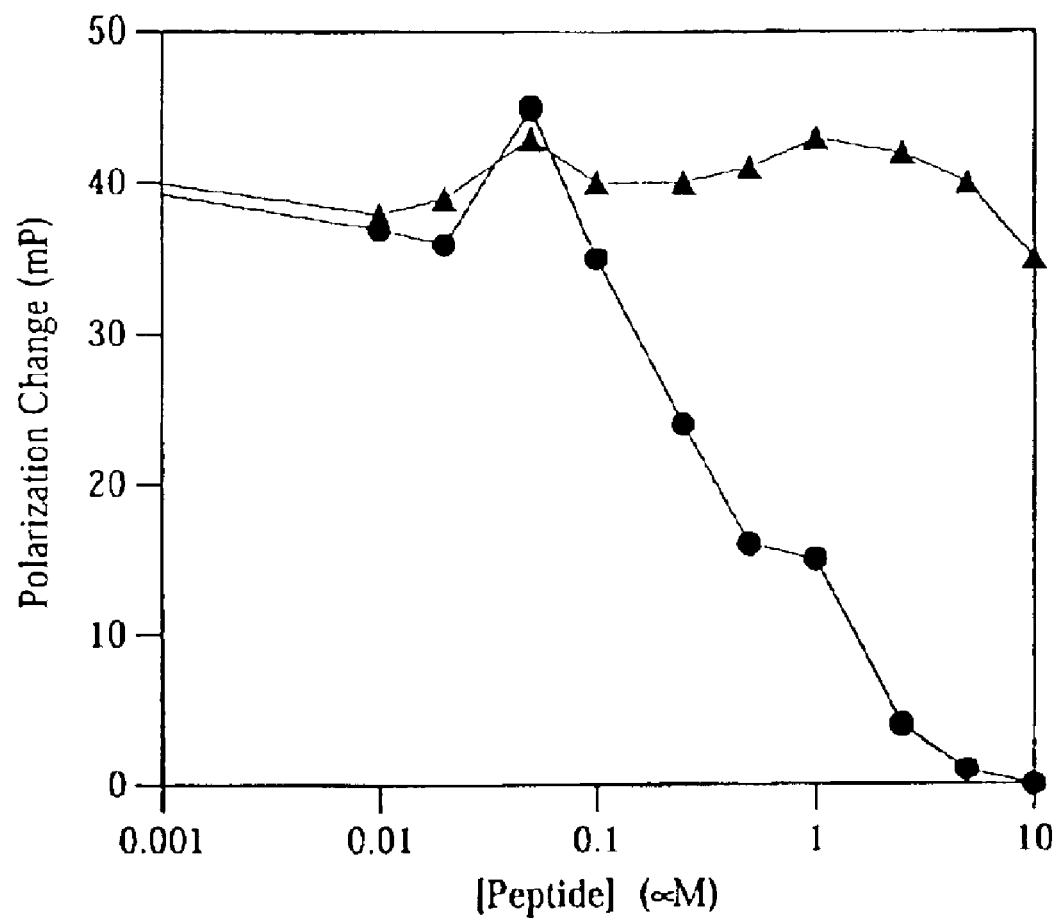

FIG. 6 is a quantitative analysis of rSdrG(50–597) binding to intact immobilized Fg or Fg peptide β1–25. FIG. 6A shows increasing concentrations of rSdrG(50–597) were incubated with the fluorescein-labeled N-terminal Bβ chain peptide β1–25 (10 nM) for 3 h in the dark at room temperature. Equation 1 was used to fit the binding data. From three experiments the $K_D$ for the interaction of rSdrG (50–597) with peptide β1–25 was calculated to be $1.4 \pm 0.01 \times 10^{-7}$ M. FIG. 6B: Binding of the fluorescein-labeled β1–25 to rSdrG(50–597) in the presence of increasing concentrations of unlabeled β1–25 (•) or the scrambled Bβ chain peptide β1–25S (▼). Values are the mean of duplicate reactions.

Figure 7:
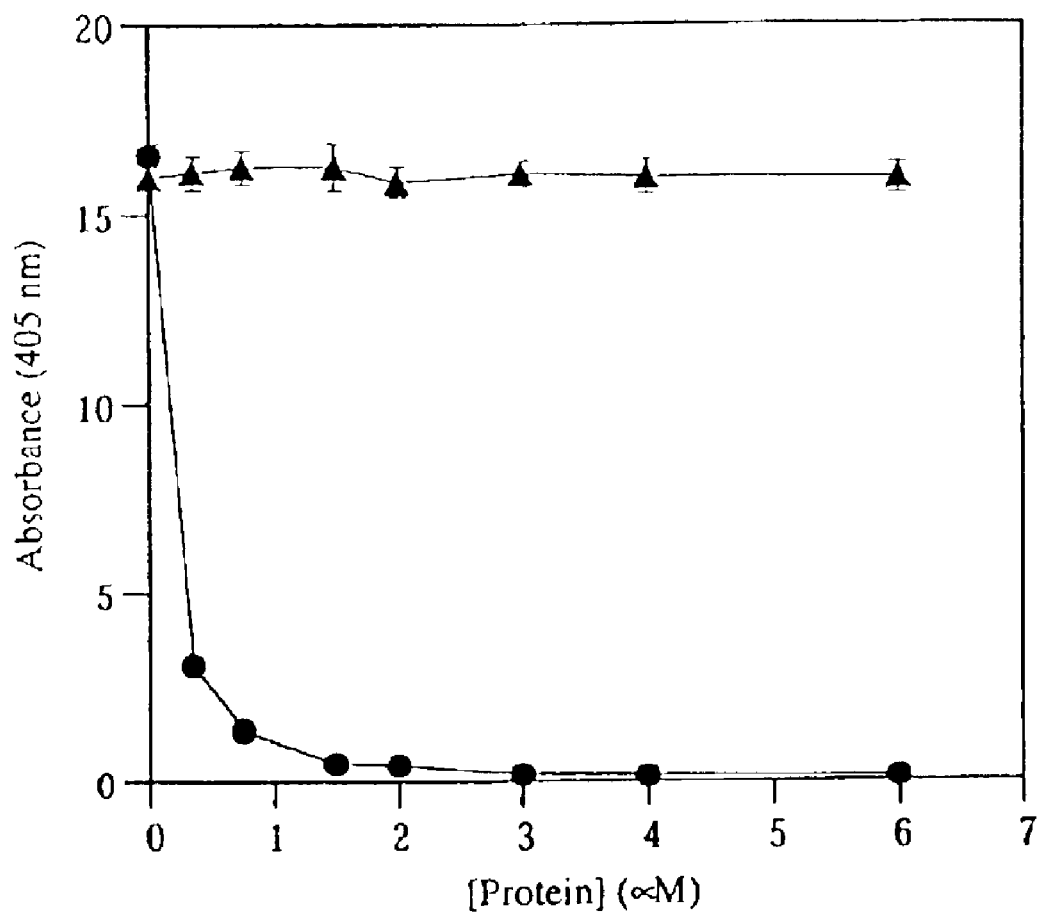

FIG. 7 shows the inhibition of fibrin clot formation by rSdrG(50–597). Thrombin (1.0 NIH unit/ml) was added to a mixture of Fg (3.0 µM) and rSdrG(50–597) (•) (0–6.0 µM) or BSA (▼) (0–6.0 µM) in microtiter wells. Fibrin clot formation was monitored by measuring an increase in optical density at 405 nm. Values represent the mean±standard deviation of quadruple wells.

Figure 8:
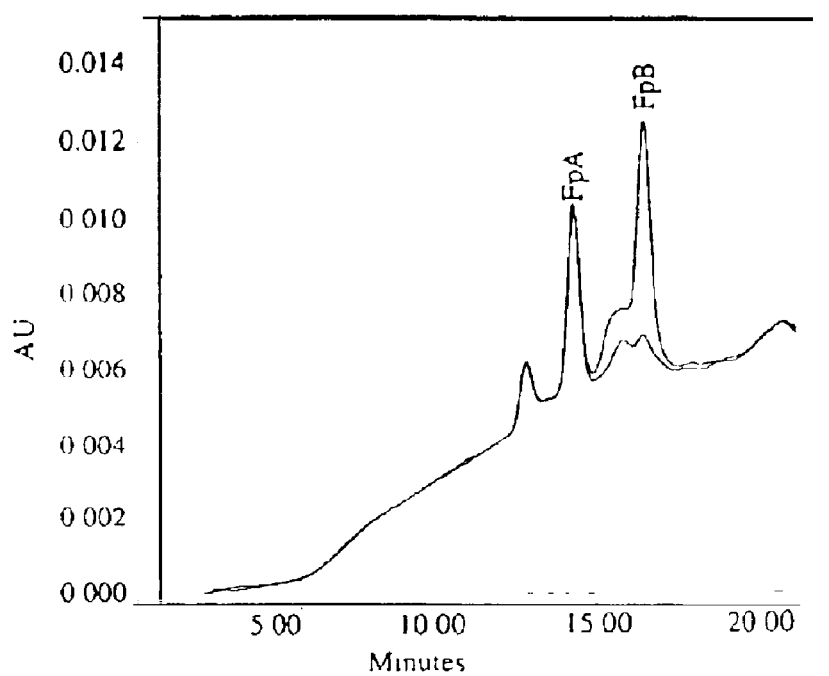

FIG. 8 shows the Inhibition of FpB release by rSdrG (50–597). Superimposed chromatograms show the amount of fibrinopeptide released when the Fg-thrombin sample has no SdrG present (upper curve) and when the Fg-thrombin sample is incubated with 1.5 µM rSdrG(50–597) (lower curve) at the 60 min time point. The decrease in the amount of FpB released with SdrG present is shown in the lower curve.

Figure 9:
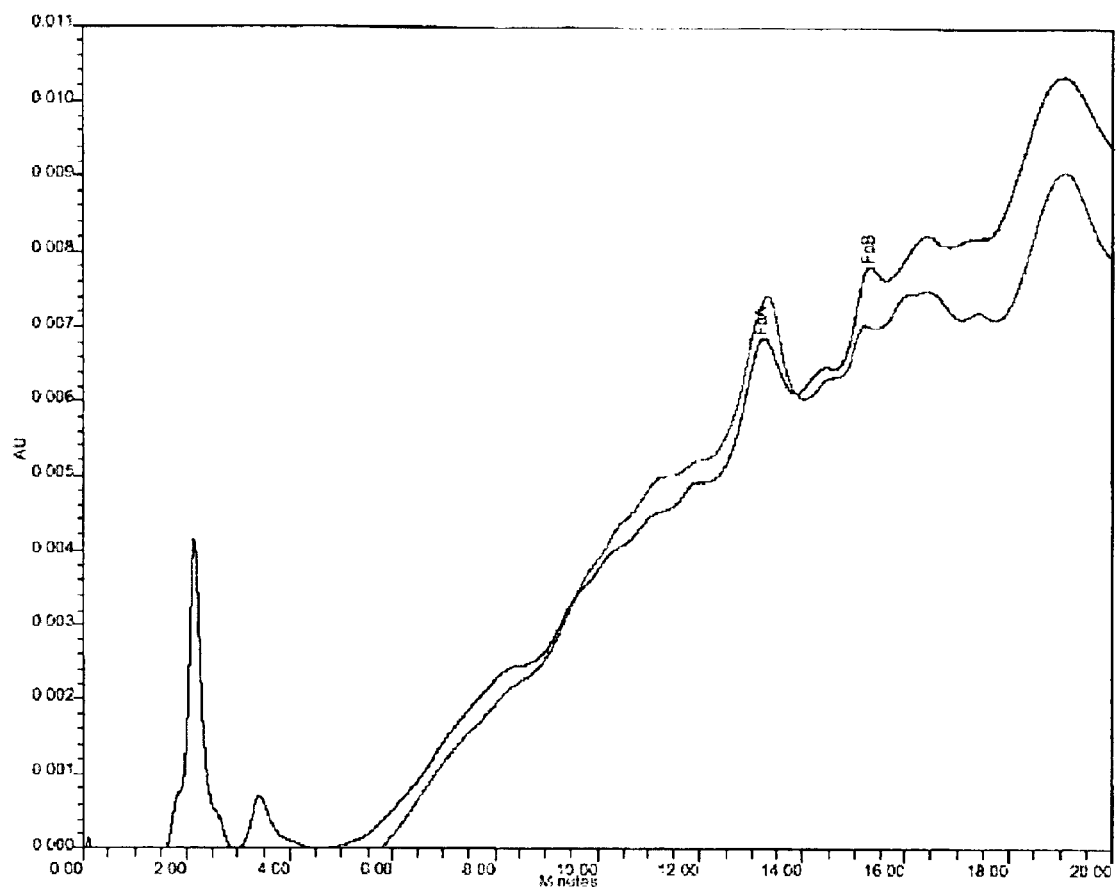

FIG. 9 shows rSdrG(50–597) binding to Serine protease-digested Fg. Fg coated microtiter wells were pretreated for 30 min at room temperature with ancrod (•), PBS (untreated) (▼), thrombin (♦) or contortrixobin (■). Plates were blocked, washed and incubated with a serine protease inhibitor (1 NIH unit/ml hirudin for thrombin and 100 µg/ml PMSF for ancrod and contortrixobin). Biotin labeled rSdrG (50–597) (25–1000 nM) was incubated in the wells for 1 h at room temperature. Values represent the mean±standard deviation of triplicate wells.

Figure 10:
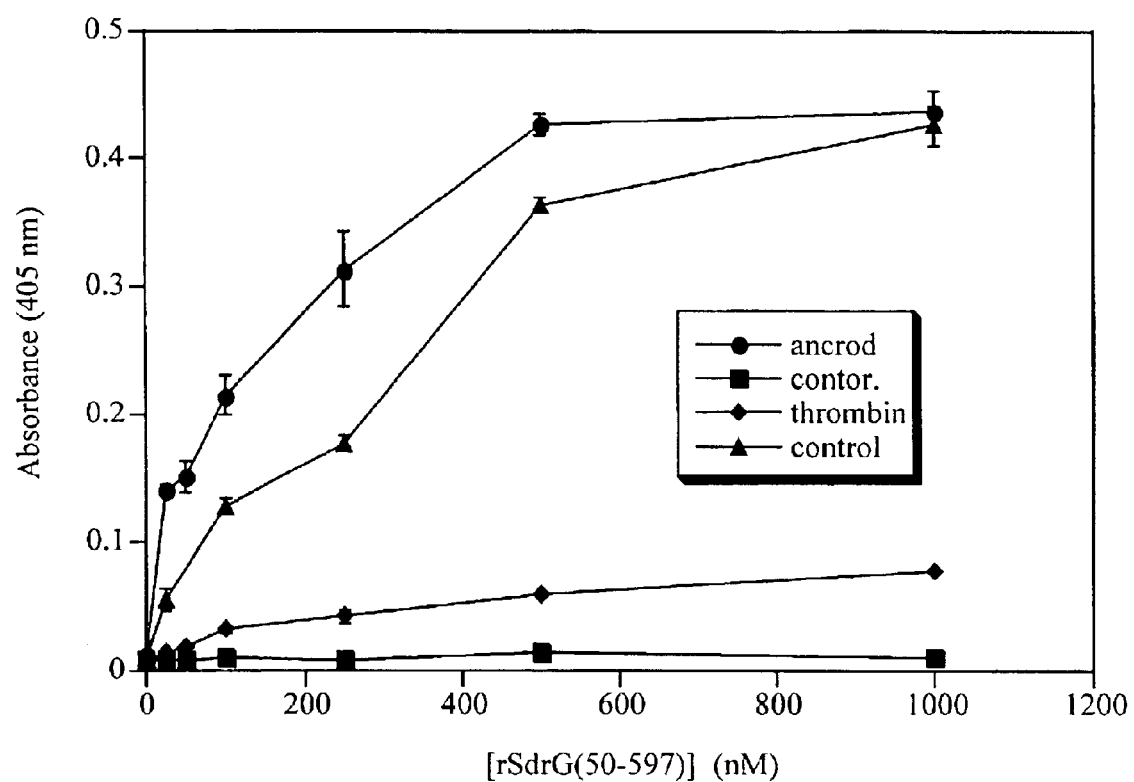

FIG. 10 shows the inhibition of FpB Release by rSdrG (50–597). Superimposed chromatograms show the amount of fibrinopeptide released when the Fg-contortrixobin sample has no SdrG present (upper curve) and when the Fg-contortrixobin sample is incubated with 1.5 µM rSdrG (50–597) (lower curve) at the 60 min time point. The decrease in the amount of FpB released with SdrG present is shown in the lower curve.

DETAILED DESCRIPTION OF THE PREFERRED EMBODIMENTS

In accordance with the present invention, there is provided a method and composition for treating or preventing thrombin-induced coagulation wherein an effective amount of SdrG which can bind the Bβ chain of fibrinogen, or its active fragments such as the A region of SdrG, is administered so as to inhibit the binding of thrombin to fibrinogen and reduce or prevent the release of fibrinopeptide B from fibrinogen and thus prevent the thrombin-induced clot formation process. In accordance with the present invention, the inventors have now localized the fibrinogen-binding site for SdrG to the Bβ chain of the N-terminal region of Fg, and more particularly to the region of from about residues 6–20 on the Fg Bβ chain which is proximal to the thrombin cleavage site. Accordingly, the present invention provides for methods of using SdrG as an anti-coagulation agent since it inhibits thrombin binding, thus preventing the cleavage and subsequent release of fibrinopeptide B which is an initial step in the initiation of the production of fibrin and the thrombin-induced formation of blood clots.

SdrG is a fibrinogen-binding protein from *S. epidermidis* which has a binding region known as the A region or A domain at residues 50–597 of the SdrG protein. Detailed information concerning SdrG and its primary binding region, known as the A domain or A region, has been disclosed in pending U.S. Ser. No. 09/386,962, filed Aug. 31, 1999, incorporated herein by reference. The SdrG protein suitable for use in the present invention, which includes binding regions of the SdrG protein including the A domain or region, may be prepared through isolation of the natural protein or binding region, or more preferably through recombinant means using nucleic acids coding for SdrG and/or its binding region A. The nucleic acid and amino acid sequences for SdrG and its binding region A have been previously disclosed in pending U.S. Ser. No. 09/386,962, filed Aug. 31, 1999 as discussed above, and these sequences may be utilized in conventional recombinant procedures in order to produce SdrG and/or its binding region A which will be suitable for use in the present invention.

In accordance with one specific embodiment of the present invention, a recombinant SdrG A region was obtained using plasmid cloning of an sdrG gene fragment. In this procedure, *Escherichia coli* strain JM101 was used for plasmid cloning. *E. coli* strain Topp3 (Stratagene) was used for protein expression. Strains harboring plasmids were grown in Lennox L broth (Sigma) or on Lennox L agar (Sigma) supplemented with 100 µg/ml ampicillin. The gene fragment encoding the entire A-region was amplified by PCR using *S. epidermidis* K28 genomic DNA as a template. The oligonucleotide primers used were 5'-CCC GGATCCGAGGAGMTACA GTACAAGACG-3' (SEQ ID NO: 2) and 5'-CCC GGTACCGATTTTTTCAGGAGGCAAGTCACC-3' (SEQ ID NO: 3). The restriction enzyme cleavage sites (underlined) BamHI and KpnI were incorporated into the forward and reverse primers, respectively. The reactions were carried out using a Perkin-Elmer DNA thermocyclcer. The reactions contained 50 ng of template DNA, 100 pmol of forward and reverse primers, 20 mM Tris-HCl (pH 8.8), 2 mM MgSO$_4$, 10 mM KCl, 10 mM (NH$_4$)$_2$SO$_4$, 0.1% Triton X-100, 25 mM of each dNTP, and 5 units of Pfu DNA polymerase (Stratagene). Amplification was performed at 94° C. for 1 min, 50° C. for 1 min, 72° C. for 4 min, for 25 cycles.

Next, the cloning of sdrG into the expression plasmid was carried out. In this process, the amplified sdrG fragment was digested with BamHI and KpnI and ligated into the expression plasmid pQE30 (Qiagen Inc.) that had been digested with the same enzymes, yielding the construct pSdrG (50–597). The recombinant protein rSdrG(50–597) expressed from this plasmid contains an N-terminal extension of six histidine residues (His-tag). Expression and purification of the recombinant protein was then obtained. In these steps, E. coli transformed with pSdrG(50–597) was grown for ~2 h for the cultures to give an $OD_{600}$ of 0.6. rSdrG(50–597) expression was induced by the addition of isopropyl-β-thiogalactopyranoside (IPTG) (Gibco-BRL) (225 μM) and the cultures were incubated at 37° C. for an additional 3 h. Bacteria were pelleted and resuspended in phosphate buffered saline (PBS), pH 7.5 (140 mM NaCl, 270 μM KCl, 430 μM $Na_2HPO_4$, 147 μM $KH_2PO_4$) and frozen o/n at −20° C.

Next, bacterial cells were thawed and mechanically lysed by using a French Pressure Cell (SLM Amnico). Cell debris was removed by centrifugation and filtration through a 0.45 μm filter membrane. The supernatant containing the recombinant protein was applied to a $Ni^{2+}$ charged (87.5 mM) 5 ml Hi Trap chelating column (Amersham Pharmacia Biotech) connected to a FPLC system. The column was equilibrated with buffer A (0.1 M NaCl, 10 mM Tris-HCl, pH 8.0) before the application of the filtered lysate. The column was then washed with 10 bed volumes of buffer A containing 5 mM imidazole. Bound protein was eluted with a continuous linear gradient of imidazole (5–120 mM; total volume 160 mls) in buffer A. Fractions were monitored for protein by determining the absorbance at 280 nm and fractions containing rSdrG(50–597) were identified by SDS-PAGE (16). These fractions were pooled and dialyzed against PBS, pH 7.5. The dialyzed protein was then applied to a Q-Sepharose column (Amersham Pharmacia Biotech) equilibrated with 25 mM Tris-HCl, pH 8.0. Bound protein was eluted with a continuous linear gradient of NaCl (0–0.5 mM; total volume 160 mls) in 25 mM Tris-HCl, pH 8.0. Fractions containing the purified rSdrG (50–597) were identified by determining the absorbance at 280 nm and by SDS-PAGE. The truncated A region of ClfA was purified as previously reported (17).

In accordance with the present invention, the SdrG proteins or SdrG A region from S. epidermidis may be utilized as compositions to treat or prevent thrombin-induced coagulation in human or animal patients, and thus to treat or prevent a wide variety of conditions associated therewith. In the preferred composition, the SdrG protein is utilized in an amount effective to treat or prevent thrombin-induced coagulation, and the composition comprises the effective amount of the SdrG protein along with a pharmaceutically acceptable vehicle, carrier or excipient as would be well known to those of ordinary skill in the art including such materials as saline, dextrose, water, glycerol, ethanol, other therapeutic compounds commonly used, and combinations thereof. As one skilled in this art would recognize, the particular vehicle, excipient or carrier used will vary depending on the nature of the patient and the patient's condition, and a variety of modes of administration would be suitable for the compositions of the invention, as would be recognized by one of ordinary skill in this art. Suitable methods of administration of any pharmaceutical composition disclosed in this application will preferably be intravenous, but other suitable methods of administering a compound for the desired purpose or preventing or reducing thrombin-induced coagulation may be introduced in other suitable ways as would be known to those of ordinary skill in this art.

As indicated above, it is preferred that the compositions and methods in accordance with the invention comprise SdrG or its A region in an amount effective to prevent or reduce thrombin-induced coagulation in the blood and thus be effective in the treatment or prevention of thrombin-induced coagulation under conditions such as venous thrombosis wherein such treatment or prevention is highly desirable. By effective amount is meant that level of use of the SdrG proteins of the present invention that will be sufficient to prevent or reduce thrombin-induced coagulation in accordance with the invention, and thus be useful in the treatment or prevention of a condition wherein thrombin-induced coagulation is sought to be prevented or alleviated. As would be recognized by one of ordinary skill in this art, the particular amount of the SdrG protein to be used in accordance with the invention to treat or prevent thrombin-induced coagulation or a condition characterized thereby will vary depending on the nature and condition of the patient, and/or the severity of the pre-existing condition to be treated or prevented, such as in an operation wherein blood coagulation is disfavored.

In accordance with the present invention, a method is thus provided for treating or preventing thrombin-induced coagulation of blood comprising administering to a human or animal patient in need thereof an SdrG protein such as the binding region A of SdrG in an amount effective to prevent or reduce thrombin-induced coagulation in the blood. The SdrG protein may be used in the form of a therapeutic, pharmaceutically-acceptable composition as described above, the amount utilized will be the amount effective in treating or preventing thrombin-induced coagulation as also described in more detail above. As also indicated above, the SdrG protein utilized in the invention is preferably a recombinant protein, and in the particularly preferred embodiment, a recombinant SdrG protein is used which constitutes the SdrG A region and which has the sequence of the residues 50–597 of SdrG. In the preferred method, the SdrG compounds and compositions of the invention are administered in any suitable way to effect introduction of the active agent into the patient's bloodstream or other applicable area in order to achieve the desired goal of reducing or preventing thrombin-induced coagulation in a human or animal patient. As one of ordinary skill in this art would recognize, this can be accomplished in a number of suitable ways, including direct intravenous or intraarterial injection, or via injection into other target areas where the anti-coagulant effects of the compositions of the invention are needed. For example, the present compositions may be utilized in the same manner that heparin is introduced into a patient to achieve anti-coagulation effects, e.g., through an intravenous injection or in other suitable ways. In the preferred method, the SdrG compositions are administered for as long as necessary to achieve the desired anti-coagulant effect as would be determined, e.g., by the physician or other health care professional administering such treatment to a patient. This could be accomplished both in the treatment of a condition wherein therapeutic anti-coagulant treatment is necessary or where preventive treatment is needed such as in an operation wherein maximization of anti-coagulative effects is desired.

Accordingly, the present invention contemplates administration of effective amounts of the fibrinogen binding compositions of the invention as necessary to achieve a result associated with the inhibition of thrombin-induced coagulation, such as the prevention or reduction in binding of thrombin to fibrinogen, the interference or inhibition of the release of fibrinopeptide B from fibrinogen, or the treatment or prevention of coagulation during a disease condition such as venous thrombosis, myocardial infarction, etc. In accordance with the present invention, it is contemplated that fibrinogen-binding proteins from *S. epidermidis* may be used to prevent or treat thrombin-induced coagulation wherein said fibrinogen-binding proteins, such as SdrG or Fbe, or their respective A domains, are capable of binding the Bβ chain of fibrinogen. More particularly, the invention contemplates that fibrinogen-binding proteins, or their active subregions such as the A domains from SdrG or Fbe, which can bind at the site from about residues 6 to 20 on the Bβ chain of fibrinogen will be useful in methods to prevent or treat thrombin-induced coagulation and the conditions associated therewith. In these methods, an effective amount of the fibrinogen-binding protein is preferably administered in order to achieve the desired result of reducing or preventing thrombin-induced coagulation, and said fibrinogen-binding proteins may be utilized in compositions containing an effective amount of the active agent along with a pharmaceutical acceptable vehicle, carrier or excipient.

The examples which follow are provided which relate to certain aspects of the present invention and which exemplify certain aspects of the present invention. However, it will be appreciated by those of skill in the art that the techniques disclosed in the examples are only exemplary of techniques associated with the present invention, and that those of ordinary skill in the art recognize that, in light of the teachings of the present specification, many changes can be made in the specific embodiments which are disclosed and still obtain a like or similar result without departing from the spirit and scope of the invention.

EXAMPLES

Example 1

Preparation of Recombinant SdrG and the Determination of its Binding Attributes in Accordance with the Present Invention

SUMMARY

*Staphylococcus epidermidis* is an important opportunistic pathogen and is a major cause of foreign body infections. We have characterized the ligand-binding activity of SdrG, a fibrinogen-binding MSCRAMM from *S. epidermidis*. Western ligand blot analysis showed that a recombinant form of the N-terminal A-region of SdrG bound to the native Bβ chain of fibrinogen (Fg) and to a recombinant form of the Bβ chain expressed in *E. coli*. By analyzing recombinant truncates and synthetic peptide mimetics of the Fg Bβ chain, the binding site for SdrG was localized to residues 6–20 of this polypeptide. Recombinant SdrG bound to a synthetic 25 amino acid peptide (β1–25) representing the N-terminus of the Fg Bβ chain with a $K_D$ of $1.4 \times 10^{-7}$ M as determined by fluorescence polarization experiments. This was similar to the apparent $K_D$ ($0.9 \times 10^{-7}$ M) calculated from an ELISA where SdrG bound immobilized Fg in a concentration dependent manner. SdrG could recognize fibrinopeptide B (residues 1–14), but with a substantially lower affinity than that observed for SdrG binding to synthetic peptides β1–25 and β6–20. However, SdrG does not bind to thrombin digested Fg. Thus, SdrG appears to target the thrombin cleavage site in the Fg Bβ chain. In fact, SdrG was found to inhibit thrombin-induced fibrinogen coagulation by interfering with fibrinopeptide B release.

Introduction

Coagulase-negative staphylococci (CNS) are important opportunistic pathogens that are particularly associated with foreign body infections in humans. *Staphylococcus epidermidis* is the most common pathogenic species of CNS[1] and accounts for 74–92% of the infections caused by this group of staphylococci (1).

[1]The abbreviations used are: CNS, coagulase-negative staphylococci, ECM, extracellular matrix, Fg, fibrinogen, MSCRAMM, microbial surface component recognizing adhesive matrix molecules, ClfA and ClfB , clumping factors A and B, FnbpA and FnbpB, fibronectin-binding proteins A and B, SdrF and SdrG, serine-aspartate repeat proteins F and G, FpA and FpB, fibrinopeptides A and B, ELISA, enzyme-linked immunosorbent assay, HPLC, high performance liquid chromatography, PCR, polymerase chain reaction, PAGE, polyacrylamide gel electrophoresis, $K_D$, equilibrium dissociation constant.

The molecular pathogenesis of most infections is complex and involves multiple microbial factors and host components, but is generally initiated by the adherence of the microbe to host tissues. Bacterial adherence involves specific surface components called adhesins. Bacterial pathogens, such as staphylococci that live in the extracellular space of the host, target extracellular matrix (ECM) components, including fibrinogen (Fg) and fibronectin, for adherence and colonization. This process is mediated by a sub-family of adhesins that have been termed MSCRAMMs (microbial surface components recognizing adhesive matrix molecules) (2). *Staphylococcus aureus* expresses multiple MSCRAMMs of which several have been characterized in some detail (For a recent review see Ref. 3).

In addition to *S. epidermidis, S. aureus* also causes serious foreign body infections. *S. aureus* appears to adhere to the biomaterial through an indirect mechanism. Upon implantation, the foreign body rapidly becomes coated with host proteins derived primarily from plasma with Fg being a dominant component. *S. aureus* appears to adhere to the absorbed proteins rather than to the biomaterial itself using adhesins of the MSCRAMM family (4,5). At least four of the *S. aureus* MSCRAMMs recognize Fg. Two of these MSCRAMMs, clumping factor A and B (ClfA , ClfB ), have Fg-binding A-regions followed by a long segment of Ser-Asp (SD) dipeptide repeats. The other two Fg-binding MSCRAMMs, contain a similar ligand binding A-region followed by a fibronectin binding motif that is repeated 5 times (6). Because the fibronectin binding activity was identified first, these two MSCRAMMs are known as fibronectin binding protein A and B (FnbpA and FnbpB) (7,8). Studies have demonstrated the importance of ClfA and ClfB in the adherence of *S. aureus* to plasma-coated biomaterials. *S. aureus* mutants deficient in one or both of these MSCRAMMs exhibited an impaired ability to adhere to plasma-coated catheters in vivo or ex vivo (9, 10).

For *S. epidermidis*, adherence to foreign bodies could involve both specific and non-specific processes. The bacteria may initially associate directly with the foreign body through non-specific interactions, while the later stages of adherence may involve more specific interactions between bacterial adhesins and host ligands. *S. epidermidis* expresses polysaccharide adhesins including PS/A and PIA, which are encoded by the ica locus (11,12). In addition, we (13) and others (14) have recently shown that *S. epidermidis* contains surface proteins structurally related to *S. aureus* MSCRAMMs. Two of these *S. epidermidis* proteins, called SdrF and SdrG, have features typical of Gram-positive bacterial proteins that are anchored to the cell wall. Both proteins show significant amino acid sequence homology to ClfA and ClfB from *S. aureus* including an ~500 amino acid long A region, a SD dipeptide repeat region and features required for cell wall anchoring, including a LPXTG motif (FIG. 1A). Recent studies by Pei, et al. suggest that an *S. epidermidis* protein called Fbe can bind Fg and specifically recognizes the Bβ chain of this molecule (15). In the current study, we have localized the SdrG binding site in the Fg Bβ chain to the N-terminal segment of this polypeptide, proximal to the thrombin cleavage site. In fact, we have demonstrated that SdrG inhibits thrombin-induced fibrin clot formation by interfering with the release of fibrinopeptide B.

Experimental Procedures

*Bacterial Strains and Growth Conditions*—*Escherichia coli* strain JM101 was used for plasmid cloning. *E. coli* strain Topp3 (Stratagene) was used for protein expression. Strains harboring plasmids were grown in Lennox L broth (Sigma) or on Lennox L agar (Sigma) supplemented with 100 μg/ml ampicillin.

PCR Amplification of the sdrG Gene Fragment—The gene fragment encoding the entire A-region was amplified by PCR using *S. epidermidis* K28 genomic DNA as a template. The oligonucleotide primers used were 5'-CCC GGATCCGAGGAGAATACA GTACAAGACG-3' (SEQ ID NO:2) and 5'-CCC GGTACCGATTTTTTCAGGAGGCAAGTCACC-3' (SEQ ID NO:3). The restriction enzyme cleavage sites (underlined) BamHI and KpnI were incorporated into the forward and reverse primers, respectively. The reactions were carried out using a Perkin-Elmer DNA thermocycler. The reactions contained 50 ng of template DNA, 100 pmol of forward and reverse primers, 20 mM Tris-HCl (pH 8.8), 2 mM $MgSO_4$, 10 mM KCl, 10 mM $(NH_4)_2SO_4$, 0.1% Triton X-100, 25 mM of each dNTP, and 5 units of Pfu DNA polymerase (Stratagene). Amplification was performed at 94° C. for 1 min, 50° C. for 1 min, 72° C. for 4 min, for 25 cycles.

Cloning of sdrG into the Expression Plasmid—The amplified sdrG fragment was digested with BamHI and KpnI and ligated into the expression plasmid pQE30 (Qiagen Inc.) that had been digested with the same enzymes, yielding the construct pSdrG(50–597). The recombinant protein rSdrG(50–597) expressed from this plasmid contains an N-terminal extension of six histidine residues (His-tag).

Expression and Purification of Recombinant MSCRAMM Protein—*E. coli* transformed with pSdrG(50–597) was grown for ~2 h for the cultures to give an $OD_{600}$ of 0.6. rSdrG(50–597) expression was induced by the addition of isopropyl-β-thiogalactopyranoside (IPTG) (Gibco-BRL) (225 μM) and the cultures were incubated at 37° C. for an additional 3 h. Bacteria were pelleted and resuspended in phosphate buffered saline (PBS), pH 7.5 (140 mM NaCl, 270 μM KCl, 430 μM $Na_2HPO_4$, 147 μM $KH_2PO_4$) and frozen o/n at –20° C. Bacterial cells were thawed and mechanically lysed by using a French Pressure Cell (SLM Amnico). Cell debris was removed by centrifugation and filtration through a 0.45 μm filter membrane. The supernatant containing the recombinant protein was applied to a $Ni^{2+}$ charged (87.5 mM) 5 ml Hi Trap chelating column (Amersham Pharmacia Biotech) connected to a FPLC system. The column was equilibrated with buffer A (0.1 M NaCl, 10 mM Tris-HCl, pH 8.0) before the application of the filtered lysate. The column was then washed with 10 bed volumes of buffer A containing 5 mM imidazole. Bound protein was eluted with a continuous linear gradient of imidazole (5–120 mM; total volume 160 mls) in buffer A. Fractions were monitored for protein by determining the absorbance at 280 nm and fractions containing rSdrG (50–597) were identified by SDS-PAGE (16). These fractions were pooled and dialyzed against PBS, pH 7.5. The dialyzed protein was then applied to a Q-Sepharose column (Amersham Pharmacia Biotech) equilibrated with 25 mM Tris-HCl, pH 8.0. Bound protein was eluted with a continuous linear gradient of NaCl (0–0.5 mM; total volume 160 mls) in 25 mM Tris-HCl, pH 8.0. Fractions containing the purified rSdrG(50–597) were identified by determining the absorbance at 280 nm and by SDS-PAGE. The truncated A region of ClfA was purified as previously reported (17).

Synthetic Peptides—The synthetic Fg peptides β1–25, β1–25S, β1–20, β6–25, were custom ordered from Research Genetics and the fibrinopeptides A and B (FpA and FpB) were from Bachem. Peptides β6–20 and β11–20 were synthesized in our laboratory using a multiple peptide synthesizer by Advanced Chemtech. For the following peptides the residue numbers are given and the sequence follows (Residue 1 corresponds to the first residue of the mature Bβ chain.): peptide β1–25, is composed of the first 25 amino acid residues of the N-terminus of the Bβ chain of Fg (QGVNDNEEGFFSARGHRPLDKK REE) (SEQ ID NO:4), peptide β1–20 (QGVNDNEEGFFSARGHRPLD) (SEQ ID NO:5), peptide β6–25 (NEEGFFSARGHRPLDKKREE) (SEQ ID NO:6), peptide β1–25S is a scrambled version of peptide β1–25 (FSERKDLHQGEGNPREFVENDAKGR) (SEQ ID NO:7), peptide β6–20 (NEEGFFSA RGHRPLD) (SEQ ID NO:8), peptide β11–20 (FSARGHRPLD) (SEQ ID NO:9), FpA (ADSEGEGDFLAEGGGVR) (SEQ ID NO:10), and FpB (QGVNDNEEGFFSAR) (SEQ ID NO:11). Peptides were purified by HPLC and analyzed by MALDI mass spectrometry.

ELISA—Microtiter plates (Immulon 4, Dynatech Laboratories Inc.) were coated with 1 μg of Fg (Enzyme Research Labs) in PBS, pH 7.5 for 18 h at 4° C. Plates were washed three times with PBS, 0.05% Tween 20 (PBST) and blocked with 1% (w/v) bovine serum albumin (BSA) for 1 h at room temperature. Plates were washed three times with PBST and rSdrG(50–597), diluted into PBS, was added to the wells and the plate was incubated for 1 h at room temperature. Plates were washed three times with PBST and bound rSdrG(50–597) was detected by adding a 1:2000 dilution of an anti-His-tag mAb (Clontech) in PBST, 0.1% BSA. Plates were incubated for 1 h at room temperature and then washed three times with PBST. A 1:2000 dilution of goat anti-mouse alkaline phosphatase (AP)-conjugated polyclonal antibodies (Bio-Rad) in PBST, 0.1% BSA were added to the wells and the plate was incubated for 1 h at room temperature. Plates were washed three times with PBST and developed with p-nitrophenyl phosphate (Sigma) in 1 M diethanolamine, 0.5 mM $MgCl_2$, pH 9.0 at room temperature for ~30 min. Plates were read at 405 nm using an ELISA plate reader (Thermomax microplate reader, Molecular Devices).

In the inhibition experiments, 50 nM rSdrG(50–597) in PBS was pre-incubated with the indicated amounts of selected peptides for 1 h at room temperature. The sample mixtures were added to the Fg-coated wells and bound rSdrG(50–597) was detected as described above.

For the ELISA with thrombin-digested Fg, the plate was coated with Fg and blocked as described above. The plate was washed three times with PBST and 50 μl of 1.0 NIH unit/ml of thrombin was added to the Fg coated wells. The plate was incubated at 37° C. for 30 min. The plate was washed three times with PBST and 50 μl of 1.0 NIH unit/ml of hirudin (Sigma) was added to the wells and incubated at 37° C. for 30 min. The plate was washed three times with PBST and blocked with 1% BSA for 1 h at room temperature. After washing three times with PBST, 100 μl of biotin labeled rSdrG(50–597) (25–1000 nM) or a rSdrG(50–597)/hirudin (1.0 NIH unit/ml) mixture was added to the wells and incubated for 1 h at room temperature. The plate was washed three times with PBST and a 1:5000 dilution of streptavidin-AP conjugated (Boehringer Mannheim) in PBST/0.1% BSA was added to the wells for 1 h at room temperature. The plate was washed three times with PBST and developed as described above.

Construction of Fg Bβ Chain Truncates—An E. coli strain harboring plasmid p668 which contains the cDNA for the Fg Bβ chain was kindly provided by Dr. Susan T. Lord (University of North Carolina, Chapel Hill, N.C.). The 1525 bp fragment from p668 was subcloned into the plasmid pQE30 to produce recombinant mature Bβ chain with a N-terminal His-tag. Additional Bβ chain constructs (FIG. 3A) were made by subcloning into either pQE30 or pGEX-KG (Pharmacia) to produce recombinant proteins with a N-terminal His-tag or Glutathione S-transferase (GST) fusion.

Western Ligand Blot Analysis—Whole E. coli lysates harboring each respective Fg Bβ chain construct were fractionated by SDS-PAGE and the separated proteins were transferred to nitrocellulose membrane with a semi-dry transfer cell (Bio-Rad). The membrane was incubated overnight with 5% (w/v) non-fat dry milk in PBS, pH 7.5 at 4° C. to saturate non-specific binding sites. After blocking, the membrane was washed three times with PBST and then incubated with biotin labeled rSdrG(50–597) (0.5 μM) for 1 h at room temperature. rSdrG(50–597) was biotin labeled using EZ Link-sulfo-NHS-LC biotin (Sigma) according to the manufacturers' instructions. After three more washes with PBST, the blot was incubated with a 1:5000 dilution of streptavidin-AP conjugated for 1 h at room temperature and developed with 5-bromo-4-chloro-3-indolyl phosphate (BCIP) and nitro blue tetrazolium (NBT) (Biorad) in carbonate:bicarbonate buffer (14 mM $Na_2CO_3$, 36 mM $NaHCO_3$, 5 mM $MgCl_2$:$6H_2O$, pH 9.8) for ~15 min at room temperature.

Fluorescence Polarization—Fluorescence polarization was used to determine the equilibrium dissociation constant ($K_D$) for the interaction of rSdrG(50–597) with peptide β1–25. The peptide was labeled with fluorescein as previously described (18). Increasing concentrations of rSdrG (50–597) in PBS, pH 7.5, were incubated with 10 nM labeled peptide for 3 h in the dark at room temperature. Reactions were allowed to reach equilibrium. Polarization measurements were taken with a Luminescence Spectrometer LS50B (Perkin Elmer) using FL WinLab software (Perkin Elmer). Binding data was analyzed by nonlinear regression used to fit a binding function as defined by the following equation:

$$\Delta P = \frac{\Delta P_{max} \cdot [\text{protein}]}{K_D + [\text{protein}]} \quad \text{Equation 1.}$$

where ΔP corresponds to the change in fluorescence polarization, $\Delta P_{max}$ is the maximum change in fluorescence, and $K_D$ is the equilibrium dissociation constant of the interaction. A single binding site was assumed in this analysis.

Fg Coagulation Assay—150 μl of a 3.0 μM Fg solution was incubated with 10 μl of rSdrG(50–597) or BSA (1.0–6.0 μM) and 50 μl of thrombin (Sigma) (1.0 NIH unit/ml) in microtiter wells at room temperature. Clot formation was monitored by measuring the increase in optical density (OD) at 405 nm over time and expressed as $V_{max}$ (mOD/min). A plate reader (Thermomax microplate reader, SOFTmax software, Molecular Devices) was used to monitor OD. Using the kinetic mode with one wavelength (L1=405 nm), samples were read every 10 sec for 5 min. In this assay, 1.0 NIH unit/ml of thrombin incubated with 3.0 μM Fg produced a fibrin clot in 5 min at room temperature.

Release of Fibrinopeptides by Thrombin—The thrombin catalyzed release of fibrinopeptides A and B was analyzed as follows. Fg solutions were diluted to 0.3 μM in 20 mM HEPES (pH 7.4), 150 mM NaCl, 5 mM ε-aminocapriotic acid, and 1.0 mM $CaCl_2$. ε-aminocapriotic acid was included to inhibit any possible plasmin contaminant activity. Thrombin was added to a final concentration of 0.05 NIH units/ml. rSdrG(50–597) was added to a final concentration of 0.3 μM, 0.6 μM, or 1.5 μM. The tubes were mixed by inversion and 500 μl aliquots were removed for the 15 and 60 min time points. The aliquots were incubated at room temperature and then immersed in boiling water for 15 min to halt the reaction. The aliquots were stored on ice for the remainder of the time course. At the end of the reaction the samples were centrifuged for 15 min at 4° C., and the supernatants were removed and stored at −20° C. overnight prior to analysis by high performance liquid chromatography.

The fibrinopeptides released were monitored by reverse phase HPLC essentially as described (19). The samples were loaded onto a Waters Delta-Pak $C_{18}$ column equilibrated with buffer A (25 mM $NaH_2PO_4$/$Na_2HPO_4$, pH 6.0). Fibrinopeptides were eluted with a linear gradient from 100% buffer A to 40% buffer B (Buffer A with 50% acetonitrile) and monitored by absorbance at 205 nm. Fibrinopeptide peak area was determined using the software Waters Millennium[32].

Results

Expression and Purification of Recombinant SdrG A-region—In order to characterize the ligand binding activity of SdrG, a recombinant form of the putative ligand binding A-region (residues 50–597) (FIG. 1C) was expressed in E. coli with a N-terminal His-tag. This protein construct, rSdrG(50–597), was purified by metal chelate affinity chromatography followed by ion-exchange chromatography. The purity of the recombinant protein was confirmed by SDS-PAGE analysis, where it migrated with an apparent molecular mass of ~97 kDa (FIG. 1B). This is larger than the theoretical molecular weight of 63.7 kDa predicted from the primary amino acid sequence of this protein. Analysis of rSdrG(50–597) by MALDI mass spectrometry indicated a molecular mass of 63.3 kDa. Aberrant migration in SDS-PAGE has also been observed with recombinant MSCRAMMs derived from S. aureus, and may be explained by the hydrophilic nature of these proteins (9,13).

SdrG Binds the Fg Bβ Chain SdrG is closely related to the recently described fibrinogen binding MSCRAMM Fbe (15). Therefore, we initially examined the ligand binding specificity of SdrG for Fg in an ELISA. In this assay, rSdrG(50–597) bound immobilized Fg, but failed to bind to other immobilized ECM proteins such as fibronectin, collagen types I and IV, vitronectin, laminin and thrombospondin (data not shown). Binding of increasing concentrations of rSdrG(50–597) to absorbed Fg exhibited saturation kinetics (FIG. 2). Together these observations demonstrate the specificity of the SdrG-Fg interaction. Furthermore, biotin labeled rSdrG(50–597) recognized the Bβ chain, but not the Aα or γ chains of Fg when analyzed by Western ligand blotting (data not shown).

Localization of the SdrG Binding Site in the Fg Bβ Chain—The observation that rSdrG binds the Fg Bβ chain fractionated under reducing and denaturing conditions in Western ligand blot analysis suggests that the MSCRAMM recognizes a specific linear amino acid sequence in the Bβ chain. To explore this possibility and locate the SdrG binding site, a recombinant mature Fg Bβ chain and a series of truncated forms of the Bβ chain expressed in *E. coli* were analyzed by Western ligand blot. The recombinant Bβ chain constructs were expressed as either His-tag or glutathione S-transferase (GST) fusion proteins (FIG. 3A). The fractionated proteins were transferred to a supporting membrane and probed with biotin labeled rSdrG(50–597) (FIG. 3B). rSdrG(50–597) recognized the mature recombinant Bβ chain (residues 1–462) as well as the recombinant truncates encompassing residues 1–341, 1–220, 1–195 and 1–95. However, rSdrG(50–597) failed to bind to the two recombinant truncates that lacked the N-terminal 25 amino acid residues of the Bβ chain, rβ(25–95) and rβ(25–195) (FIG. 3B). These observations demonstrate that rSdrG(50–597) recognizes a linear sequence in Fg and suggests that this site lies within the N-terminal region of the Bβ chain.

Inhibition of rSdrG(50–597) Binding to Fg by Synthetic Peptides—To further define the rSdrG(50–597) binding site in the Fg Bβ chain, we used a peptide mimetic approach. A series of peptides representing segments of the N-terminal region of the FgBβ chain were synthesized and tested for their ability to inhibit the binding of rSdrG(50–597) to Fg in an ELISA (FIG. 4). In FIG. 4A, peptides β1–25 and β6–25 were shown to inhibit the binding of rSdrG(50–597) to Fg in a concentration dependent manner, whereas the scrambled version of β1–25, peptide β1–25S, did not interfere with the binding of rSdrG(50–597) to Fg. Effective inhibition of rSdrG(50–597) binding to Fg was also observed with peptide β6–20 and, to a somewhat lesser degree, with β1–20. Peptide β11–20 was essentially inactive in this assay (FIG. 4B).

The thrombin cleavage sites in Fg lie between residues 14 (Arg) and 15 (Gly) in the Bβ chain and between 16 (Arg) and 17 (Gly) in the Aα chain. Upon cleavage of Fg by thrombin the fibrinopeptides, FpA and FpB, are sequentially released. The fibrinopeptides were examined as inhibitors of rSdrG(50–597) binding to Fg in an ELISA. FpB inhibited the binding of rSdrG(50–597) in a concentration dependent manner, but this peptide was at least 10 fold less active than the synthetic peptide β1–25 (FIG. 4C). FpA was essentially inactive and behaved similar to the scrambled peptide β1–25S. Taken together, this suggest that rSdrG(50–597) recognizes a linear amino acid sequence in the Bβ chain located within residues 6–20. This recognition site appears to overlap the thrombin cleavage site in this polypeptide.

rSdrG Binding to Thrombin-Digested Fg—The rSdrG binding site seems to lie within close proximity to the thrombin cleavage site, therefore, we investigated if rSdrG (50–597) could bind to Fg in which the thrombin cleavage site was abolished. Fg coated microtiter wells were pretreated with thrombin or thrombin plus hirudin (which inhibits thrombin activity) in order to remove FpB and destroy the cleavage site. The ability of rSdrG(50–597) to bind to this thrombin digested Fg was significantly impaired (FIG. 5), suggesting that the thrombin cleavage site residues Bβ 14 (Arg), 15 (Gly) and residues within FpB (1–14) are essential for rSdrG(50–597) to bind Fg.

Determination of Equilibrium Dissociation Constants ($K_D$)—An equilibrium dissociation constant ($K_D$) for the interaction of rSdrG(50–597) with the Fg Bβ chain peptide β1–25 was determined. By analyzing the binding of increasing concentrations of rSdrG(50–597) to the fluorescein-labeled β1–25 peptide in a fluorescence polarization assay, rSdrG(50–597) binding to the labeled peptide exhibited saturation kinetics with a $K_D$ of $1.4\pm0.01\times10^{-7}$ M (FIG. 6A). To demonstrate the specificity of this interaction, the binding of rSdrG(50–597) to the labeled β1–25 peptide was measured in the presence of increasing amounts of unlabeled peptide (β1–25) or scrambled peptide (β1–25S). The unlabeled β1–25 peptide, but not peptide β1–25S inhibited binding of rSdrG(50–597) to the fluorescein-labeled β1–25 peptide, in a concentration dependent manner (FIG. 6B). The apparent $K_D$ determined for the binding of rSdrG (50–597) to the fluorescein labeled peptide β1–25 is similar to the apparent $K_D$ ($0.9\times10^{-7}$ M) for the interaction of rSdrG(50–597) with immobilized, intact Fg as determined by ELISA (FIG. 2).

rSdrG(50–597) Inhibits Thrombin-Induced Fibrin Clot Formation—In the final stages of the blood coagulation cascade, thrombin cleaves Fg releasing the fibrinopeptides and producing fibrin monomers. These fibrin monomers then polymerize to form a fibrin clot (20). The localization of the SdrG binding site described above raises the possibility that rSdrG(50–597) may be able to inhibit thrombin-induced fibrin clot formation, perhaps by directly competing with thrombin for binding to the N-terminus of the Bβ chain of Fg or by binding to a proximal site and sterically blocking thrombin's proteolytic attack on the Bβ chain. To test this hypothesis, we designed a fibrin clot inhibition assay in which 3.0 μM Fg, 0–6.0 μM rSdrG(50–597) and 1.0 NIH unit/ml of thrombin were incubated and the formation of a fibrin clot was monitored by measuring the increase in optical density at 405 nm. FIG. 7 shows that rSdrG(50–597) inhibited fibrin clot formation in a concentration dependent manner, whereas BSA had no effect. This suggests that rSdrG(50–597) can interfere with thrombin activity by binding to a site in the Fg Bβ chain that is proximal to or overlaps the binding site for thrombin.

Analysis of Fibrinopeptide B Release by HPLC—The release of FpA and FpB from the N-terminus of the Aα and Bβ chains of Fg by thrombin can be monitored and quantitated by high performance liquid chromatography (19,21, 22). We examined the effect of rSdrG(50–597) on fibrinopeptide release by measuring the peak areas of FpA and FpB, as detected by HPLC. The HPLC chromatograms shown in FIG. 8 show the expected fibrinopeptide release following digestion of Fg with thrombin superimposed with the fibrinopeptide release when Fg and thrombin are incubated with rSdrG(50–597). A significant decrease in the amount of FpB release was shown with a 1:1 ratio of rSdrG(50–597) to Fg (Table I) whereas, a 5:1 ratio was effectively able to inhibit the release of FpB (FIG. 8). This effect was seen at an incubation time of 15 min and 60 min. There was no apparent interference of FpA release by rSdrG(50–597).

TABLE I

Percentage of FpB released in the presence of SdrG
Fg (0.3 μM) was incubated with SdrG and 0.5 NIH units/ml of thrombin at room temperature and the samples were analyzed by HPLC. The amount of fibrinopeptide released was determined by measuring the area under the peaks on the HPLC chromatograms. The data was normalized in order to compare the data from separate chromatograms assuming that the release of FpA is not affected by the presence of SdrG. The peak area representing FpB in the absence of SdrG was set to 100%.

| SdrG:Fg | 15 min | 60 min |
| --- | --- | --- |
| 0:1 | 100 | 100 |
| 1:1 | 65.4 | 45.2 |
| 2:1 | 13.9 | 17.4 |
| 5:1 | <0.001 | <0.001 |

Discussion

In this study, we have shown that SdrG binds the N-terminus of the Bβ chain of Fg with a high degree of specificity. The binding of SdrG to an N-terminal Fg peptide exhibits a $K_D$ of $1.4\times10^{-7}$ M, which is significantly lower than the $K_D$ determined for the binding of ClfA to a γ chain peptide ($2.0\times10^{-5}$ M) (18). Thus, SdrG appears to have a higher affinity for its respective synthetic Fg peptide target compared to the S. aureus MSCRAMM. The $K_D$ determined for the binding of SdrG to the synthetic peptide β1–25 is similar to the apparent $K_D$ estimated for the binding of SdrG to intact Fg absorbed onto microtiter wells. This observation suggests that the SdrG binding site in the synthetic peptide is presented in a nearly optimal form and that additional segments of Fg do not significantly contribute to the formation of the SdrG binding site.

Several studies have examined the role of Fg binding MSCRAMMs from S. aureus as virulence factors in animal models. Strains in which the genes encoding ClfA or ClfB have been inactivated are less virulent compared to the wild type strain in a rat model of catheter-induced endocarditis (23,24). These results suggest that ClfA- and ClfB-mediated adherence is required for the maximum virulence potential of S. aureus to be expressed. ClfB has been shown to promote S. aureus adherence to ex vivo hemodialysis tubing, further confirming that ClfB contributes to bacterial attachment to biomaterials coated with host proteins (9). In a recent study, Stutzmann Meier, et al. showed that heterologous expression of ClfA on Streptococcus gordonii, which is generally considered a non-virulent bacterium, rendered this organism pathogenic in a rat endocarditis model (25). With the discovery that SdrG is a Fg binding MSCRAMM expressed by S. epidermidis, the possibility arises that SdrG can act as a virulence factor in S. epidermidis-induced infections and plays a role similar to that of the Fg binding MSCRAMMs in S. aureus-induced infections.

We have mapped the binding site of rSdrG(50–597) in the Fg Bβ chain to a linear sequence in the N-terminal region of this polypeptide. Peptide β6–20 is a potent inhibitor of the binding of rSdrG(50–597) to Fg, whereas FpB (1–14) has poor inhibitory activity. Because peptide β6–20, but not β11–20 is recognized by this MSCRAMM, the N-terminal border of the binding site must lie between residues 6 and 11 of the Bβ chain. The observation that rSdrG(50–597) is unable to bind to thrombin digested Fg, i.e. the fibrinopeptides are absent, suggests that the C-terminus of this binding site is located between residues 14 and 20 of the Bβ chain.

It is striking that many of the identified staphylococcal MSCRAMMs appear to specifically recognize Fg, although the sites targeted in Fg by these proteins vary. ClfA, FnbpA and FnbpB of S. aureus all recognize the C-terminus of the Fg γ chain (6,27). ClfB from S. aureus targets an as yet unidentified site in the Aα chain (9) and SdrG is here shown to bind to the N-terminus of the Bβ chain. Thus, these MSCRAMMs use a conserved A region to bind different sites in Fg. Furthermore, the MSCRAMMs appear to target sites in Fg that are important in the molecular physiology of this key component of hemostasis. The C-terminus of the γ chain is recognized by the platelet integrin $\alpha_{IIb}\beta_3$ and ClfA is a potent inhibitor of Fg-induced platelet aggregation (26,27). Here, we show that the binding site in the Bβ chain for rSdrG(50–597) appears to overlap the thrombin cleavage site and that rSdrG(50–597) can interfere with fibrin clot formation by inhibiting the thrombin-induced release of FpB. Fg may play an important role in the host's defense against microbial infections and interfering with this function gives the bacteria an advantage and the ability to survive in a hostile environment. One such potential advantage may be related to the observed chemotactic activity of FpB for human peripheral blood leukocytes (28–30). We have shown that rSdrG(50–597) can prevent the release of FpB, thus one can speculate that the reason S. epidermidis possesses a protein that can bind to this region of the Fg Bβ chain is to prevent the release of chemotactic elements. This may reduce the influx of phagocytic neutrophils and help to ensure the survival of the bacteria in the host.

References

The following articles are incorporated herein by reference:

1. Garrett, D. O., Jochimsen, E., Murfift, K., Hill, B., McAllister, S., Nelson, P., Spera, R. V., Sall, R. K., Tenover, F. C., Johnston, J., Zimmer, B., and Jarvis, W. R. (1999) Infect Control Hosp Epidemiol 20(3), 167–70.
2. Patti, J. M., and Höök, M. (1994) Curr Opin Cell Biol 6(5), 752–8
3. Foster, T. J., and Höök, M. (1998) Trends Microbiol 6(12), 484–8
4. Galliani, S., Viot, M., Cremieux, A., and Van der Auwera, P. (1994) J Lab Clin Med 123(5), 685–92.
5. Vaudaux, P., Pittet, D., Haeberli, A., Huggler, E., Nydegger, U. E., Lew, D. P., and Waldvogel, F. A. (1989) J Infect Dis 160(5), 865–75.
6. Wann, E. R., Gurusiddappa, S., and Höök, M. (2000) J Biol Chem 275(18), 13863–71.
7. Flock, J. I., Fröman, G., Jonsson, K., Guss, B., Signas, C., Nilsson, B., Raucci, G., Höök, M., Wadstrom, T., and Lindberg, M. (1987) Embo J 6(8), 2351–7.
8. Fröman, G., Switalski, L. M., Speziale, P., and Höök, M. (1987) J Biol Chem 262(14), 6564–71
9. Ni Eidhin, D., Perkins, S., Francois, P., Vaudaux, P., Höök, M., and Foster, T. J. (1998) Mol Microbiol 30(2), 245–57
10. Vaudaux, P. E., Francois, P., Proctor, R. A., McDevitt, D., Foster, T. J., Albrecht, R. M., Lew, D. P., Wabers, H., and Cooper, S. L. (1995) Infect Immun 63(2), 585–90
11. McKenney, D., Hubner, J., Muller, E., Wang, Y., Goldmann, D. A., and Pier, G. B. (1998) Infect Immun 66(10), 4711–20
12. Cramton, S. E., Gerke, C., Schnell, N. F., Nichols, W. W., and Götz, F. (1999) Infect Immun 67(10), 5427–33.
13. McCrea, K. W., Hartford, O., Davis, S., Ni Eidhin, D., Lina, G., Speziale, P., Foster, T. J., and Höök, M. (2000) Microbiology 146(Pt 7), 1535–46.
14. Nilsson, M., Frykberg, L., Flock, J. I., Pei, L., Lindberg, M., and Guss, B. (1998) Infect Immun 66(6), 2666–73
15. Pei, L., Palma, M., Nilsson, M., Guss, B., and Flock, J. I. (1999) Infect Immun 67(9), 4525–30
16. Laemmli, U. K. (1970) Nature 227, 680–685
17. McDevitt, D., Francois, P., Vaudaux, P., and Foster, T. J. (1995) Mol Microbiol 16(5), 895–907.
18. O'Connell, D. P., Nanavaty, T., McDevitt, D., Gurusiddappa, S., Höök, M., and Foster, T. J. (1998) J Biol Chem 273(12), 6821–9.
19. Mullin, J. L., Gorkun, O. V., Binnie, C. G., and Lord, S. T. (2000) J Biol Chem 275(33), 25239–46.
20. Herrick, S., Blanc-Brude, O., Gray, A., and Laurent, G. (1999) Int J Biochem Cell Biol 31(7), 741–6
21. Ng, A. S., Lewis, S. D., and Shafer, J. A. (1993) Methods Enzymol 222, 341–58
22. Haverkate, F., Koopman, J., Kluft, C., D'Angelo, A., Cattaneo, M., and Mannucci, P. M. (1986) Thromb Haemost 55(1), 131–5.
23. Moreillon, P., Entenza, J. M., Francioli, P., McDevitt, D., Foster, T. J., Francois, P., and Vaudaux, P. (1995) Infect Immun 63(12), 4738–43

24. Entenza, J. M., Foster, T. J., Ni Eidhin, D., Vaudaux, P., Francioli, P., and Moreillon, P. (2000) *Infect Immun* 68(9), 5443–6.
25. Stutzmann Meier, P., Entenza, J. M., Vaudaux, P., Francioli, P., Glauser, M. P., and Moreillon, P. (2001) *Infect Immun* 69(2), 657–664.
26. Farrell, D. H., Thiagarajan, P., Chung, D. W., and Davie, E. W. (1992) *Proc Natl Acad Sci U S A* 89(22), 10729–32.
27. McDevitt, D., Nanavaty, T., House-Pompeo, K., Bell, E., Turner, N., McIntire, L., Foster, T., and Höök, M. (1997) *Eur J Biochem* 247(1), 416–24
28. Kay, A. B., Pepper, D. S., and McKenzie, R. (1974) *Br J Haematol* 27(4), 669–77.
29. Richardson, D. L., Pepper, D. S., and Kay, A. B. (1976) *Br J Haematol* 32(4), 507–13.
30. Senior, R. M., Skogen, W. F., Griffin, G. L., and Wilner, G. D. (1986) *J Clin Invest* 77(3), 1014–9.

Example 2

Experiments Showing SdrG Inhibits Serine Protease Digestion of Human Fibrinogen

The localization of the binding site for SdrG in Fg revealed that the thrombin cleavage site was in close proximity to the SdrG binding site. We were able to show that SdrG could not bind to thrombin-treated Fg but could, in fact, inhibit thrombin-catalyzed fibrin clot formation. In a related study, we analyzed SdrG for its ability to bind to immobilized Fg that had been treated with other serine proteases isolated from snake venom and for its ability to inhibit clot formation in the presence of these same proteases. The fibrinolytic activities of snake venoms have been well documented and their activities are similar to thrombin, however, some may be specific for the Aα chain or the Bβ chain only. In this study we employed three proteases from snake venoms that have different activities. Ancrod, an α-fibrinogenase isolated from *Calloselasma rhodostoma* (Malayan Pit viper), releases only FpA and leads to the formation of an unstable fibrin clot (Bell 1997). Contortrixobin, a β-fibrinogenase isolated from *Agkistrodon contortrix contortrix* (Southern Copperhead) preferentially releases FpB but does not form a clot effectively because FpA has not been released.

Results

SdrG Binding to Serine Protease-treated Immobilized Fg—In an ELISA similar to the ELISA experiment described previously, we found that rSdrG(50–597) could not bind to Fg treated with thrombin or contortrixobin, the β-fibrinogenase but could bind to untreated Fg. rSdrG (50–597) could actually bind better to Fg treated with ancrod, the α-fibrinogenase, than to untreated Fg (FIG. 9). The AD chain may interfere with rSdrG(50–597) binding to the Bβ chain and this observation may be due to the absence of FpA, thus making the N-terminus of the Bβ chain more easily accessible.

Analysis of Fibrinopeptide B Release by HPLC—As in chapter two, we monitored the fibrinopeptide release in the presence of SdrG and the β-fibrinogenase contortrixobin. The HPLC chromatograms shown in FIG. 10 show the expected fibrinopeptide release following digestion of Fg with contortrixobin superimposed with the fibrinopeptide release when Fg and contortrixobin are incubated with rSdrG(50–597). A decrease in the amount of FpB release is seen when a 1:5 ratio of Fg to rSdrG (50–597) is used. The amount of FpB released with contortrixobin is significantly less than the amount released with thrombin. This is most likely because FpA is still intact on the Fg molecule, thus contortrixobin is not as effective at cleaving Fg due to steric hindrance from FpA.

Discussion

The results of this study with serine proteases isolated from snake venoms corroborate the results seen with SdrG and thrombin. rSdrG(50–597) was not able to bind to Fg that was treated with a different protease that preferentially cleaves the FpB from the Bβ chain. This eliminates any concern that the effect seen with thrombin-treated Fg was in any way due to thrombin inhibiting rSdrG(50–597) from binding. Because rSdrG(50–597) was still able to bind to ancrod-treated Fg this also confirms that the FpA from the Aα chain was not involved in SdrG binding to Fg.

rSdrG(50–597) was able to effectively inhibit FpB release in the presence of the β-fibrinogenase contortrixobin supporting the evidence that was shown previously and substantiating the mechanism by which SdrG is inhibiting clot formation is in fact by inhibiting FpB release. We were, however, unable to perform the clot inhibition experiment shown in chapter two due to the ineffective clot formation when only FpB is released, thus there was no accurate control.

Interestingly, ancrod has been used clinically as an antithrombotic agent for a number of different disease conditions including stroke, myocardial infarction, sickle-cell crisis and venous thrombosis[1] (Forbes 1993; Atkinson 1997) (Gilles, Reid et al. 1968), (Davies, Merrick et al. 1972). This defibrinating enzyme cleaves FpA, but not FpB from Fg to form a clot that is very sensitive to endogenous fibrinolysis, additionally ancrod activates plasminogen further contributing to fibrinolysis (Pizzo, Schwartz et al. 1972; Carr 1975; Bell 1997). The result of administering ancrod is a significant reduction in plasma Fg concentration within minutes and within hours the level of Fg is markedly depressed. Hypofibrinogenemia is sustained by administering ancrod daily. After termination of treatment, the plasma Fg rises gradually, returning to normal levels in days (Bell, Bolton et al. 1968). The limited clinical experience indicates that defibrination is achieved with ancrod with reasonable safety, however, the elaboration of neutralizing antibodies with repeated injections of ancrod leads to resistance (Pitney, Holt et al. 1969; Pitney and Regoeczi 1970), (Vinazzer 1973; Sapru, Moza et al. 1975).

[1]Definitions: venous thrombosis—the presence of a blood clot within a vein, hypofibrinogenemia—abnormal deficiency of fg in the blood, thrombocytopenia—persistent decrease in the number of blood platelets.

SdrG inhibits clot formation by preventing the release of FpB. Although the mechanism of thrombosis prevention by SdrG is different than that of ancrod, the ability of SdrG to inhibit clot formation could potentially lead to its use as a novel anti-thrombotic agent. Certainly, much more research would be needed to reliably assess its effectiveness and safety relative to heparin. Heparin is the standard treatment for thrombotic disorders and its mode of action is by increasing the effectiveness of anti-thrombin III. A potentially important indication for ancrod and possibly SdrG may be to avoid heparin-induced thrombocytopenia, resulting from heparin treatment. In addition, since SdrG binds to the Bβ chain of Fg, it may be possible to also use it in conjunction with other agents, such as ancrod, which target the Aα chain of Fg in order to further enhance the anticoagulation when necessary. If used in this fashion, in addition to a composition of SdrG used to reduce or prevent thrombin-induced coagulation, ancrod in an amount effective to interfere or inhibit the release of fibrinopeptide A from fibrinogen may also be administered along with the SdrG.

All of the references disclosed herein are incorporated by reference.

What is claimed is:

1. A method of inhbiting thrombin-induced coagulation of blood in a human or animal patient in need thereof comprising administering to said human or animal patient a *S. epidermidis* fibrinogen-binding protein that can bind to the fibrinogen Bβ chain in an amount effective to inhibit thrombin-induced coagulation.

2. A method according to claim 1 wherein the fibrinogen-binding protein is selected from the group consisting of SdrG, Fbe, the SdrG A domain and the fbe A domain.

3. A method according to claim 1 wherein the fibrinogen-binding protein binds at the site of residues 6–20 of the fibrinogen Bβ chain.

4. A method of inhibiting thrombin-induced coagulation of blood in a human or animal patient in need thereof comprising administering to said human or animal patient an SdrG serine-aspartate repeat protein in an amount effective to inhibit thrombin-induced coagulation of the blood.

5. The method according to claim 1 wherein the SdrG protein is the ligand-binding A region of SdrG.

6. The method according to claim 2 wherein the A region has the sequence of residues 50–597 of SdrG.

7. The method according to claim 1 wherein the SdrG protein is a recombinant protein.

8. The method according to claim 1 wherein the method is used in conjunction with treatment of a disease condition selected from the group consisting of stroke, myocardial infarction, sickle-cell crisis and venous thrombosis.

9. The method according to claim 1 wherein the method is used to reduce the concentration of plasma fibrinogen in the patient's blood.

10. The method according to claim 1 wherein the method is used to inhibit the release of fibrinopeptide B from fibrinogen.

11. The method according to claim 1 further comprising the step of administering ancrod in an amount effective to inhibit the release of fibrinopeptide A from fibrinogen.

12. A method of inhibiting thrombin binding to fibrinogen comprising administering to a human or animal patient in need thereof an SdrG protein in an amount effective to inhibit thrombin binding to fibrinogen.

13. A method of inhibiting the release of fibrinopeptide B from fibrinogen comprising administering to a human or animal patient in need thereof an SdrG protein in an amount effective to inhibit the release of fibrinopeptide B from fibrinogen.

* * * * *